(12) United States Patent
Gruaz et al.

(10) Patent No.: US 9,809,624 B2
(45) Date of Patent: Nov. 7, 2017

(54) NEUROTENSIN ANALOGUES FOR RADIOISOTOPE TARGETING TO NEUROTENSIN RECEPTOR-POSITIVE TUMORS

(75) Inventors: Anne Gruaz, Paris (FR); Didier Pelaprat, Paris (FR); Jacques Barbet, Nantes (FR); Dirk Tourwe, Brussels (BE)

(73) Assignees: INSERM (Institut National de la Sante et de la Recherche Medicale), Paris (FR); IASON GmbH, Graz-Seiersberg (AT)

( * ) Notice: Subject to any disclaimer, the term of this patent is extended or adjusted under 35 U.S.C. 154(b) by 824 days.

(21) Appl. No.: 13/384,418

(22) PCT Filed: Jul. 16, 2010

(86) PCT No.: PCT/EP2010/060293
§ 371 (c)(1),
(2), (4) Date: May 1, 2012

(87) PCT Pub. No.: WO2011/006985
PCT Pub. Date: Jan. 20, 2011

(65) Prior Publication Data
US 2012/0207676 A1 Aug. 16, 2012

(30) Foreign Application Priority Data
Jul. 16, 2009 (EP) .................................... 09305679

(51) Int. Cl.
*A61K 51/00* (2006.01)
*A61M 36/14* (2006.01)
*C07K 7/08* (2006.01)
*A61K 51/08* (2006.01)
*A61K 38/00* (2006.01)

(52) U.S. Cl.
CPC .............. *C07K 7/083* (2013.01); *A61K 51/08* (2013.01); *A61K 51/085* (2013.01); *A61K 51/088* (2013.01); *A61K 38/00* (2013.01)

(58) Field of Classification Search
CPC ........ A61K 38/00; A61K 51/00; A61K 51/08; A61K 51/088; A61K 51/085; C07K 7/83; C07K 14/00; C07K 14/78; C07K 7/06; C07K 14/005; C07K 7/083
USPC ........... 424/1.11, 1.65, 1.69, 9.1; 514/1, 1.1, 514/21.3, 21.7, 21.8; 530/300, 328, 329; 435/7.23
See application file for complete search history.

(56) References Cited

U.S. PATENT DOCUMENTS

| | | | | |
|---|---|---|---|---|
| 4,110,321 A | * | 8/1978 | Folkers | 530/327 |
| 5,952,464 A | * | 9/1999 | Mertens et al. | 530/329 |
| 6,214,790 B1 | * | 4/2001 | Richelson et al. | 514/4.8 |
| 6,312,661 B1 | * | 11/2001 | Reubi | A61K 51/088 424/1.41 |
| 7,015,306 B2 | * | 3/2006 | Srinivasan | A61K 47/48276 424/9.1 |
| 2009/0062212 A1 | * | 3/2009 | Richelson | C07K 7/083 514/1.1 |

FOREIGN PATENT DOCUMENTS

WO 0078796 A2 12/2000
WO 0130398 A2 5/2001

OTHER PUBLICATIONS

De Visser M et al: "Stabilised 111 In-labelled DTPA- and DOTA-conjugated neurotensin analogues for imaging and therapy of exocrine pancreatic cancer", European Journal of Nuclear Medicine and Molecular Imaging Aug. 2003, vol. 30, No. 8, Aug. 2003 (Aug. 2003), pp. 1134-1139, XP002568443.
Janssen Paul J J M et al: "Five stabilized (111)in-labeled neurotensin analogs in nude mice bearing HT29 tumors" Cancer Biotherapy & Radiopharmaceuticals, vol. 22, No. 3, Jun. 2007 (Jun. 2007), pp. 374-381, XP002568444.
Achilefu Samuel et al: "Novel bioactive and stable neurotensin peptide analogues capable of delivering radiopharmaceuticals and molecular beacons to tumors." Journal of Medicinal Chemistry, vol. 46, No. 15, Jul. 17, 2003 (Jul. 17, 2003) , pp. 3403-3411, XP002568445.
Maes Veronique et al: "Novel Tc-99m-labeled neurotensin analogues with optimized biodistribution properties" Journal of Medicinal Chemistry, vol. 49, No. 5, Mar. 2006 (Mar. 2006), pp. 1833-1836, XP002568446.
Garcia-Garayoa E et al: "Doubl e-stabllized neurotens in analogues as potential radiopharmaceuticals for NTR-positive tumors", Nuclear Medicine and Biology, vol. 33, No. 4, May 1, 2006 (May 1, 2006), pp. 495-503, XP025103552.
Elisa Garca AA-Garayoa et al: "A stable neurotensin-based radiopharmaceutical for targeted imaging and therapy of neurotensin receptor-positive tumours" European Journal of Nuclear Medicine and Molecular Imaging, vol. 36, No. 1, Aug. 9, 2008 (Aug. 9, 2008) , pp. 37-47, XP019654484.
Alshoukr Paisal et al: "Novel Neurotensin Analogues for Radioisotope Targeting to Neurotensin Receptor-Positive Tumors" Bioconjugate Chemistry, vol. 20, No. 8, Aug. 2009 (Aug. 2009), pp. 1602-1610, XP00256844.
International Search Reported, dated Sep. 10, 2010, in PCT/EP2010/060293.

* cited by examiner

*Primary Examiner* — D L Jones
(74) *Attorney, Agent, or Firm* — Young & Thompson (57) ABSTRACT

The invention relates to a new neurotensin analogue, or a salt thereof, useful for targeting to neurotensin receptor-positive tumors, like ductal pancreatic adenocarcinoma, exocrine pancreatic cancer, invasive ductal breast cancers, colon adenocarcinoma, small cell lung carcinoma, Ewing sarcoma, meningioma, medulloblastoma and astrocytoma.

11 Claims, 3 Drawing Sheets

SEQUENCE LISTING

<160> NUMBER OF SEQ ID NOS: 2

<210> SEQ ID NO 1
<211> LENGTH: 13
<212> TYPE: PRT
<213> ORGANISM: Homo sapiens

<400> SEQUENCE: 1

Glu Leu Tyr Glu Asn Lys Pro Arg Arg Pro Tyr Ile Leu
1               5                   10

<210> SEQ ID NO 2
<211> LENGTH: 6
<212> TYPE: PRT
<213> ORGANISM: Artificial
<220> FEATURE:
<223> OTHER INFORMATION: neurotensin fragment

<400> SEQUENCE: 2

Arg Arg Pro Tyr Ile Leu
1               5

NEUROTENSIN ANALOGUES FOR RADIOISOTOPE TARGETING TO NEUROTENSIN RECEPTOR-POSITIVE TUMORS

FIELD OF THE INVENTION

The invention relates to compounds targeting metal isotopes to neurotensin receptor-positive tumors.

BACKGROUND OF THE INVENTION

Pancreatic adenocarcinoma, the tenth most common human cancer, grows extremely rapidly, disseminates early and occult metastases are frequent. Non invasive staging modalities have shown limited ability to detect local invasion or small volume metastatic disease. $^{18}$F-labeled 2-deoxy-2-fluoro-D-glucose ($^{18}$F-FDG), which has greatly improved the diagnosis and staging of numerous tumors, does not significantly increase the accuracy of preoperative determination of resectability of pancreatic adenocarcinoma. Therefore, a non invasive method to improve preoperative staging would be extremely useful.

Indisputable success of scintigraphy and radiotherapy of neuroendocrine tumors has been obtained with somatostatin analogues labeled with radiometals, such as $^{111}$In, $^{68}$Ga, $^{90}$Y or $^{177}$Lu. PET imaging with $^{68}$Ga potentially provides higher diagnostic efficacy than SPECT. Therapy with $^{90}$Y or $^{177}$Lu affords symptomatic improvement, prolonged survival and better quality of life in some instances. However, somatostatin analogs only bind tumors that express somatostatin receptors.

It has been shown that 75-88% ductal pancreatic adenocarcinoma express neurotensin (NT) receptors, but little or no somatostatin receptors. NT receptors have been proposed as new markers for this tumor since they were not detected in normal pancreas and chronic pancreatitis. NT receptors were also identified in other tumor cells as, for example, Ewing's sarcoma, meningiomas, small cell lung carcinoma and colon adenocarcinoma. In patients with invasive ductal breast cancers, 91% of tumors are positive for the neurotensin high-affinity receptor (NTSR1), while it is poorly expressed or absent in normal cells (Souaze et al., *Cancer Res*. (2006) 66, 6243-6249). This recent work points out the diagnostic and therapeutic potential of molecules targeting NTSR1 receptor.

Neurotensin, the natural ligand for neurotensin receptors, is a thirteen amino acid peptide, isolated from bovine hypothalamus and has the following structure: pGlu-Leu-Tyr-Glu-Asn-Lys-Pro-Arg-Arg-Pro-Tyr-Ile-Leu-OH.

Examples of neurotensin analogues bearing a chelating moiety suitable for labeling with technetium or rhenium may be found in the literature, e.g. Garcia-Garayoa et al., *Eur J Nucl Med Mol Imaging*, (2009) 36(1), p. 37-47).

Acyclic or macrocyclic poly(aminocarboxylate) compounds are suitable chelators for radioisotopes such as $^{111}$In, $^{67}$Ga, $^{68}$Ga, $^{90}$Y, $^{86}$Y, $^{177}$Lu, $^{212}$Bi, $^{213}$Bi, $^{64}$Cu, $^{67}$Cu, $^{44}$Sc, $^{44m}$Sc, $^{47}$Sc. To target NTSR1 positive tumors, neurotensin ligands bearing acyclic or macrocyclic poly(aminocarboxylate) chelators such as DTPA or DOTA have thus been developed (de Visser et al., *Eur. J. Nucl. Med. Mol. Imaging*. (2003), 30, 1134-1139; Janssen et al., *Cancer Biother Radiopharm*. (2007), 22(3), 374-381; Hillairet de Boisferon et al., *Bioconjug. Chem*. (2002), 13, 654-662).

The efficiency of a compound targeting neurotensin receptor-positive tumors may be quantified by several criteria:

tumor uptake must be as high as possible, to allow their good detection or treatment;

tumor to normal tissue uptake ratios must be as high as possible, to achieve good contrasts in imaging and to minimize the irradiation of normal tissue during treatment.

If some technetium or rhenium-labeled neurotensin analogues may be considered as reasonably good according to these criteria, neurotensin analogues bearing acyclic or macrocyclic poly(aminocarboxylate) chelating agent, such as DTPA, DOTA or one of their derivatives, described so far have shown lower tumor uptake, higher kidney accumulation or both.

Here is provided new poly(aminocarboxylate) neurotensin analogues providing higher tumor uptake and/or higher tumor to normal tissue uptake ratios, particularly higher tumor to kidneys uptake ratio, than poly(aminocarboxylate) neurotensin analogues previously described in the literature. This is particularly important at early time points after activity injection (preferably before 24 hours post-injection), so that:

high contrast images may be recorded before radioactive decay of the radionuclide reduces imaging sensitivity, and exposure of normal tissues—which is also maximum at early time points is reduced.

SUMMARY OF THE INVENTION

The invention relates to a neurotensin analogue, or a salt thereof, of formula (I)

$$X\text{-}L\text{-}Aa8\text{-}Aa9\text{-}Aa10\text{-}Aa11\text{-}Aa12\text{-}Aa13 \quad (I)$$

wherein

Aa8 is selected from the group consisting of Arg, Lys, NMe-Arg, NMe-Lys, Gly(PipAm), Ala(PipAm), Phe(4-Gu), hAla(PipAm), Aba(Apy) and β-homoArg, Aa9 is selected from the group consisting of Arg, Lys, NMe-Arg, NMe-Lys, ψ(CH$_2$—NH)-Arg, ψ(CH$_2$—NH)-Lys, Gly(PipAm), Ala(PipAm) and Phe(4-Gu), Aa10 is selected from the group consisting of (L)Pro and thioproline, Aa11 is selected from the group consisting of (L)Tyr, (D)Tyr, Dmt, (L)Trp, (D)Trp, (L)Phe, (D)Phe, 2'Br-Tyr, 2'Br-Phe, (L)erythro-βMe-Tyr, (L)threo-βMe-Tyr, (L)mTyr, (D)mTyr, (L)7-HO-Tic, NaI, (L)Tcc and L-neoTrp, Aa12 is selected from the group consisting of Ile, Tle, Val and Leu, Aa13 is selected from the group consisting of Leu, tBuAla, Cha and Cpa, X represents a poly(aminocarboxylate) chelating moiety, L represents a linker which separates X and Aa8, and wherein said linker L separates X and Aa8 by a chain of at least 9 consecutive chemical bonds, said analogue, when in solution at physiological pH and at physiological temperature, has at most two positive charges, and Aa8-Aa9-Aa10-Aa11-Aa12-Aa13 differs from Arg-Arg-Pro-Tyr-Ile-Leu by at least two differences in the amino acid sequence.

The invention also relates to a pharmaceutical composition comprising a compound according to the invention and a pharmaceutically acceptable carrier.

The invention also relates to a neurotensin analogue according to the invention, further comprising a detectable element which forms a complex with the poly(aminocarboxylate) chelating moiety X. Said detectable elements is preferably selected from the group consisting of $Gd^{3+}$, $Eu^{3+}$, $^{111}In$, $^{67}Ga$, $^{68}Ga$, $^{89}Zr$, $^{64}Cu$ and $^{44}Sc$.

According to the invention, the number of positive charges of the analogue does not take into account the positive charges of said detectable element.

The invention further relates to a neurotensin analogue comprising a detectable element according to the invention for use in a diagnostic method practiced on the human or animal body, and preferably in a diagnostic method of the presence of a tumor expressing neurotensin receptor 1. According to an embodiment of the invention, said method comprises the step of detecting the presence of a tumor expressing neurotensin receptor 1.

The present invention provides a method of detecting a tumor expressing a neurotensin receptor, neurotensin receptor 1 (NTSR1) in particular, in the body of a subject, to which a quantity sufficient for imaging of a neurotensin analogues comprising a detectable element has been previously administered, comprising the step of subjecting said body to imaging.

The invention further relates to a method of in vitro diagnostic of a tumor expressing a neurotensin receptor, neurotensin receptor 1 (NTSR1) in particular, comprising the step of detecting with a neurotensin analogue comprising a detectable element according to the invention, the presence of a tumor expressing a neurotensin receptor, neurotensin receptor 1 (NTSR1) in particular, in a sample obtained from a subject.

Further, the invention also relates to a neurotensin analogue comprising a cytotoxic element which forms a complex with the chelating moiety X. Said cytotoxic elements is preferably selected from the group consisting of $^{90}Y$, $^{177}Lu$, $^{67}Cu$, $^{47}Sc$, $^{212}Bi$, $^{213}Bi$, $^{226}Th$, $^{111}In$ and $^{67}Ga$.

According to the invention, the number of positive charges of the analogue does not take into account the positive charges of said cytotoxic element.

The invention further relates to a neurotensin analogue comprising a cytotoxic element according to the invention for use in a treatment of the human or animal body by therapy. According to an embodiment of the invention, said treatment is the treatment of a tumor expressing neurotensin receptor 1.

The present invention provides a method of treating a tumor expressing a neurotensin receptor, neurotensin receptor 1 (NTSR1) in particular, in the body of a subject, comprising the step of administering to said subject an effective amount of the neurotensin analogues comprising a cytotoxic element according to the invention.

Said tumor expressing neurotensin receptor 1 (NTSR1) may be, for example, a ductal pancreatic adenocarcinoma tumor, an exocrine pancreatic cancer tumor, an invasive ductal breast cancer tumor, a colon adenocarcinoma tumor, a small cell lung carcinoma tumor, an Ewing sarcoma tumor, a meningioma tumor, a medulloblastoma tumor and an astrocytoma tumor.

DEFINITIONS

Naturally occurring neurotensin has the formula:

As used herein, the term "neurotensin analogue" covers all chemically modified derivatives of the naturally occurring neurotensin which have selective affinity to Neurotensin Receptor 1 (NTSR1), said derivatives being substituted by an X-L moiety.

The modifications by reference to the original chemical structure of naturally occurring neurotensin may be:
a) one or more amino acids have been omitted,
b) one or more amino acids have been replaced by one or more other amino acids, these amino acids being standard amino acids or amino acid mimics,
c) one or more amino acids have been functionalized.

The neurotensin analogues may have the following modifications: none; a; b; c; a and b; a and c; b and c; or a, b and c.

The neurotensin analogue may be linear or cyclic.

As used herein, a "selective affinity to NTSR1" means an affinity, when evaluated by the measure of IC 50 value for binding to HT29 cells, as described in the examples, lower than 100 nM, preferably lower than 50 nM. "IC 50" means the concentration of unlabeled drug that produces radioligand binding half way between the total binding of the radiotracer and the lower plateau of the curve describing the binding of the radioligand in presence of increasing concentrations of the unlabeled drug. Total binding means the binding of the radiotracer in the absence of the unlabeled drug.

As used herein, "standard amino acids" designates the twenty amino acids which are encoded by the standard genetic code. Standard amino acids are α-amino acids and their absolute configuration is L.

As used herein, an "amino acid mimic" designates a non-standard amino acid which has a substantially similar size and shape as a standard amino acid. Typically, the amino acid mimic can have modified side chain(s), a D absolute configuration, different side chain(s) or additional side chain(s) relative to a standard amino acid. For example, 2',6'-dimethyltyrosine is an amino acid mimic relative to tyrosine, and β-homo-arginine an amino acid mimic relative to arginine.

Initials and acronyms used herein have the conventional meaning well-known to the skilled person. Typically, "NMe-Arg" means arginine with an N-methylated bond between arginine and the preceding amino acid, "NMe-Lys" means lysine with an N-methylated bond between lysine and the preceding amino acid, "ψ(CH2-NH)-Arg" means arginine with a reduced bond between arginine and the preceding amino acid, "ψ(CH2-NH)-Lys" means lysine with an reduced bond between lysine and the preceding amino acid, "Gly(PipAm)" means 4-piperidinyl-(N-amidino)-S-glycine, "Ala(PipAm)" means 4-piperidinyl-(N-amidino)-L-alanine, "Phe(4-Gu)" means 4-guanido-L-phenylalanine, "hAla(PipAm)" means 4-piperidinyl-(N-amidino)-L-homoalanine, "Aba(Apy)" means 2-amino-4[(2-amino)-pyrimidinyl]butanoic acid, "β-homoArg" means β-homo-arginine, "thioproline" means thiazolidine-4-carboxylic acid, "Dmt" means 2',6'-dimethyltyrosine, "2'Br-Phe" means 2'-bromo-phenylalanine, "2'Br-Tyr" means 2'-bromo-tyrosine, "erythro-βMe-Tyr" means erythro-(2S,3S and 2R,3R)-β-methyltyrosine, "threo-βMe-Tyr" means threo-(2S,3R and 2R,3S)-β-methyltyrosine, "mTyr" means L-meta-tyrosine, "7-HO-Tic" means 7-hydroxy-1,2,3,4-tetrahydroisoquinoline-3-carboxylic acid, "Tcc" means 1,2,3,4-tetrahydro-2-carboline-3-carboxylic acid, "neoTrp" means 3-(4-indolyl)alanine, "Tle" means tert-leucine, "Nal" means naphtyl, "tBuAla" means tert-butyl-L-alanine, "Cpa" means cyclopentyl-L-alanine, "Cha" means cyclohexyl-L-alanine, "ACA" means L-azetidine-2-carboxylic acid, "Ahx" means aminohexanoic acid.

As used herein, "linker" designates any chemical moiety which is chemically coupled to X and Aa8, and which spaces the chelating moiety away from a portion of a peptide. Typically, the "linker" may be a combination of standard amino acids, of amino acid mimics, and of non-amino acid moieties.

As used herein, the term "chelating moiety" designates any chemical moiety which is able to form a complex with a detectable or cytotoxic element.

As used herein, a "detectable element" designates an element which exhibits a property detectable in conventional preferably human diagnostic techniques. The term "detecting" as used herein includes qualitative and/or quantitative detection (measuring levels) with or without reference to a control and the generation of images of the distribution of the detecting element in the animal or human body.

As used herein, a "cytotoxic element" designates an element which exhibits the property of being toxic to living cells.

As used herein, the terms "treatment", "treating" and the like are intended to mean obtaining a desired pharmacologic and/or physiological effect, such as inhibition of cancer cell growth or induction of apoptosis of a cancer cell, or killing cancer cells. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes: (a) preventing the recurrence of a disease or condition (e.g., preventing cancer recurrence) from occurring in an individual who has been treated for the disease but has not yet been diagnosed as having a recurrence; (b) inhibiting the disease, (e.g., arresting its development and/or curing it); or (c) relieving the disease (e.g., reducing symptoms associated with the disease).

As used herein, the terms "administering" and "administration" are intended to mean a mode of delivery including, without limitation, parenteral, subcutaneous, intravenous, intraperitoneal, intraarterial, intracavitary, rectal or intravesical.

As used herein, the term "therapeutically effective" is intended to mean an amount of a compound sufficient to substantially improve some symptom associated with a disease or a medical condition. Preferably, by "therapeutically effective", it is meant an amount of a compound sufficient to substantially improve tumor regression (which can be measured thanks to the RECIST—Response Evaluation Criteria in Solid Tumors—criteria) and/or to maintain stabilization and/or to substantially decrease cancer progression speed and/or to substantially improve survival without tumor progression and/or to substantially improve overall survival.

For example, in the treatment of cancer, a compound which decreases, prevents, delays, suppresses, or arrests any symptom of the disease would be therapeutically effective. To be considered therapeutically effective, the administered amount of a compound does not necessarily cure a disease, but provides a treatment for a disease such that the onset of the disease is delayed, hindered, or prevented, or the disease symptoms are ameliorated, or the term of the disease is changed or, for example, is less severe or recovery is accelerated in an individual. It will be understood that a specific "effective amount" for any particular individual will depend upon a variety of factors including the activity of the specific compound employed, the age, body weight, general health, sex, and/or diet of the individual, time of administration, route of administration, rate of excretion, drug combination and the severity of the particular disease undergoing prevention or therapy.

As used herein, "pharmaceutically acceptable carrier" includes any and all solvents (such as phosphate buffered saline buffers, water, saline), dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in therapeutic compositions is contemplated. Supplementary active ingredients can also be incorporated into the compositions.

DETAILED DESCRIPTION OF THE INVENTION

The compound according to the invention provides higher tumor uptake and/or higher tumor to normal tissue uptake ratios than poly(aminocarboxylate) neurotensin analogues previously described in the literature. The compounds were evaluated with regard to binding affinity, stability to enzymatic degradation, internalization rate and biodistribution.

Concerning the binding affinity of the neurotensin analogue, it is well known that the sequence NT(8-13), i.e. $Arg^8$-$Arg^9$-$Pro^{10}$-$Tyr^{11}$-$Ile^{12}$-$Leu^{13}$, is the minimal sequence that mimics the effects of full length NT (Granier et al., Eur. J. Biochem. (1982) 124, 117-124). The inventors have found that the introduction of a poly(aminocarboxylate) chelating moiety, coupled to the alpha $NH_2$, results in an important loss of affinity. The inventors have found from the results described in the example section that this loss of affinity may be minimized by increasing the distance between the chelating moiety and the amino acid sequence.

The neurotensin analogue according to the invention comprises a chelating moiety X and a linker L which separates X and Aa8, said linker L separates X and Aa8 by a chain of at least 9 consecutive bonds, typically at least 10, typically at least 11, typically at least 12.

Typically L has no positive charge. Typically in order to avoid positive charges, if L comprises amino-acid, such as Lysine, the amino-acid may be modified (e.g. by acetylation, other possible modifications leading to the neutralization of a positive charge are well known to those skilled in the art).

Typically, X and Aa8 are separated by a chain of between 9 and 24 consecutive bonds.

According to an embodiment, the linker L is -Aa6-Aa7-.

According to another embodiment, the linker L is -L1-Aa6-Aa7-.

According to another embodiment, the linker L is R-Aa6(L1)-Aa7-, wherein L1 is coupled to Aa6 via the lateral chain of Aa6 and R is a group which neutralizes the positive charge of the α-$NH_2$ function of Aa6, typically R is an acetyl group. Typically R may also be an amino-acid sequence of 1 to 3 residues, preferably the N-terminal end of the amino-acid sequence is acetylated. Typically R has no positive charge, and if R is cleaved in vivo, the resulting group linked to Aa8 is not positively charged.

According to another embodiment, the linker L is -L1-Aa6-.

According to another embodiment, the linker L is -L1-Aa7-.

According to another embodiment, the linker L is -L1-.

In these different embodiments:

Aa6 is a standard amino acid or an amino acid mimic, without positive charges. More specifically, Aa6 may be selected from the group consisting of (D)Lys, (L)Lys, (L) or (D) lysine mimic, and (L) or (D) amino acids having a function on the lateral chain allowing the coupling of L1.

Aa7 may be selected from the group consisting of (L)Pro, (D)Pro and ACA, preferably Aa7 is (L)Pro.

L1 is a linker which is chemically coupled to X and Aa6, Aa7 or Aa8, and thereby spaces the chelating moiety away from Aa8. L1 may be a natural or a non natural aminoacid or an aminoacid sequence of natural and non natural aminoacids, a diacidic spacer or any spacer containing functions which allow the coupling of L1 to Aa6 or Aa7 or Aa8 and to X which are known to those skilled in the art.

L1 may be for example —NH—$(CH_2)_n$—CO— wherein n is 1 to 10, —CO—$(CH_2)_n$—CO— wherein n is, preferably 1 to 10, or —NH—$(CH_2)_n$—NH— wherein n is preferably 1 to 10.

Typically, L1 may be coupled to Aa6 or Aa7 or Aa8 and to X via an amide bond (NH—CO), via an urea bond (NH—CO—NH) or via a thio-urea bond (NH—CS—NH).

Typically L1 may be coupled to Aa6 via the lateral chain of Aa6. Alternatively L1 may be coupled to Aa6, Aa7 or Aa8 via the α-$NH_2$ function of the amino-acid.

A high binding affinity may be not enough for a neurotensin analogue to be efficient. Since NT is rapidly degraded in vivo by peptidases, changes may be introduced to protect the three major sites of enzymatic cleavage, the $Arg^8$-$Arg^9$, $Pro^{10}$-$Tyr^{11}$ and $Tyr^{11}$-$Ile^{12}$ bonds, to stabilize these molecules (Garcia-Garayoa et al., *Nucl. Med. Biol.* (2001) 28, 75-84). Possible sequence modifications are well-known by the skilled person. However, some sequence modifications induce a loss of affinity of the sequence. The influence on affinity of most of the sequence modifications has been studied (Bruehlmeier et al., *Nucl. Med. Biol.* (2002) 29, 321-327; Garcia-Garayoa et al., *Eur. J. Nucl. Med. Mol. Imaging.* (2009) 36, 37-47; Maes et al., *J. Med. Chem.* (2006) 49, 1833-1836). Sequence modifications may increase the in vitro and in vivo stability to enzymatic degradation. In vivo stability has a major impact on tumor uptake.

The inventors have found that increasing the distance between the chelating moiety and the amino acid sequence associated to one sequence modification was not sufficient to obtain an efficient in vivo tumor targeting.

The neurotensin analogue according to the invention comprises an amino acid sequence Aa8-Aa9-Aa10-Aa11-Aa12-Aa13, which differs from Arg-Arg-Pro-Tyr-Ile-Leu by at least two differences in the amino acid sequence. By difference in the amino-acid sequence, it is meant that the sequence differs from the one of the original neurotensin sequence at a given position either by difference in the amino acid side chain or by a modification in the main chain. The amino acids Aa8 to Aa13 and the bonds between these amino acids are selected from the groups as previously defined with the proviso that at least two amino acids are not selected equal to those of the naturally occurring amino acids, i.e. Arg for Aa8, Arg for Aa9, Pro for Aa10, Tyr for Aa11, Ile for Aa12, Leu for Aa13 and amide bonds between these amino acids.

In an embodiment of the invention, the neurotensin analogue has the formula (I)

X-L-Aa8-Aa9-Aa10-Aa11-Aa12-Aa13      (I)

wherein

Aa8 is selected from the group consisting of Arg, Lys, NMe-Arg and NMe-Lys, preferably Aa8 is NMe-Arg, Aa9 is selected from the group consisting of Arg, Lys, NMe-Arg and NMe-Lys, preferably Aa9 is selected from the group consisting of Arg and Lys, and if Aa8 is NMe-Arg or NMe-Lys, Aa9 is preferably Arg or Lys, Aa10 is Pro, Aa11 is selected from the group consisting of Tyr and Dmt, Aa12 is selected from the group consisting of Ile and Tle, preferably Aa12 is Tle, Aa13 is Leu, X represents a poly(aminocarboxylate) chelating moiety, L represents a linker which separates X and Aa8, and wherein said linker L separates X and Aa8 by a chain of at least 9 consecutive bonds, said analogue, when in solution in pure water at 37° C. at pH 7, has at most two positive charges, and Aa8-Aa9-Aa10-Aa11-Aa12-Aa13 differs from Arg-Arg-Pro-Tyr-Ile-Leu by at least two differences in the amino acid sequence.

Preferably, the neurotensin analogue according to the invention, or the salt thereof, has the above technical features and is of formula (I) above, wherein Aa8 is NMe-Arg, Aa9 is Arg, Aa10 is Pro, Aa11 is selected from the group consisting of Tyr and Dmt, Aa12 is selected from the group consisting of Ile and Tle, preferably Aa12 is Tle, and Aa13 is Leu.

Further, to provide higher tumor to normal tissue uptake ratios, the biodistribution of the compound according to the invention has to be improved. It is already known that charge and charge distribution of radiolabeled peptides may produce various effects on renal uptake, but in general it is increased by positive charges (Akizawa et al., *Nucl. Med. Biol.* (2001) 28, 761-768; Froidevaux et al., *J. Nucl. Med.* (2005) 46, 887-895).

Therefore, the analogue according to the invention has at most two positive charges. If the compound comprises more than two positive charges, exceeding charges may be chemically neutralized. Typically, the N-terminal end of the peptide may be used for the coupling of the chelating moiety. Else, the N-terminal end of the molecule may be acetylated. In particular, if the chelating moiety X is coupled to an amino acid trough a function on its lateral chain, the N-terminal end of the molecule may be acetylated. Other possible modifications are known to those skilled in the art.

In addition, the inventors have found that kidney uptake may be ascribed to increased reabsorption of charged radiolabeled metabolites which are released after the cleavage of the neurotensin analogue.

The analogue according to the invention may be protected in order to avoid the formation of metabolites containing the chelating moiety and bearing more than two positive charges after cleavage of a peptide bond.

Further, the compounds according to the invention comprise a chelating moiety which is able to form a complex with a detectable element or with a cytotoxic element.

Suitable detectable elements include for example:

heavy elements or rare earth ions as used in computer axial tomography scanning (CAT scan or CT scan), paramagnetic ions as used in NMR imaging (e.g. $Gd^{3+}$, $Fe^{3+}$, $Mn^{2+}$ and $Cr^{2+}$), fluorescent metal ions (e.g. $Eu^{3+}$), and radionuclides, particularly γ-emitting radionuclides (e.g. $^{111}$In and $^{67}$Ga) as used in planar imaging and single photon emission computed tomography (SPECT, or less commonly, SPET), positron-emitting radionuclides as used in positron emission tomography (PET) (e.g. $^{68}$Ga, $^{89}$Zr, $^{64}$Cu and $^{44}$Sc).

More particularly, suitable radionuclides include those which are useful in diagnostic techniques. The radionuclides advantageously have a half-life of from 1 hour to 40 days, preferably from 5 hours to 4 days, more preferably from 12 hours to 4 days. Examples are radioactive isotopes of Indium and Gallium, e.g. $^{111}$In and $^{68}$Ga.

Suitable cytotoxic elements which are useful in therapeutic applications include $\beta^-$-emitting radionuclides, e.g. $^{90}$Y, $^{177}$Lu, $^{67}$Cu and $^{47}$Sc, α-emitting radionuclides, e.g. $^{212}$Bi, $^{213}$Bi and $^{226}$Th, and Auger-electron-emitting radionuclides, e.g. $^{111}$In and $^{67}$Ga.

According to the nature of the detectable or cytotoxic element which is complexed to the compound according to the invention, the chelating moiety X is selected from the group consisting of physiologically acceptable chelating groups capable of complexing said detectable or cytotoxic element.

The chelating moiety X is a poly(aminocarboxylate). It may be for example:
i) diethylenetriamine pentaacetic acid (or DTPA) and its derivatives, e.g.:
S-2-(4-Aminobenzyl)-diethylenetriamine pentaacetic acid (or p-NH2-Bn-DTPA),
(R)-2-Amino-3-(4-aminophenyl)propyl]-trans-(S,S)-cyclohexane-1,2-diamine-pentaacetic acid (or p-NH2-CHX-A"-DTPA),
[(R)-2-amino-3-(4-isothiocyanatophenyl)propyl]-trans-(S,S)-cyclohexane-1,2-diamine-pentaacetic acid (or CHX-A"-DTPA),
2-(4-Isothiocyanatobenzyl)-diethylenetriaminepentaacetic acid (or p-SCN-Bn-DTPA),
ii) 1,4,7,10-tetraazacyclododecane-1,4,7,10-tetraacetic acid (or DOTA) and its derivatives, for example:
S-2-(4-aminobenzyl)-1,4,7,10-tetraazacyclo-dodecane tetraacetic acid (or p-aminobenzyl-DOTA),
S-2-(4-Isothiocyanatobenzyl)-1,4,7,10-tetraazacyclododecane-tetraacetic acid (or p-SCN-Bn-DOTA),
iii) 1,4,7-triazacyclononane-1,4,7-triacetic acid (or NOTA) and its derivatives, for example:
S-2-(4-aminobenzyl)-1,4,7-triazacyclononane-1,4,7-triacetic acid (or p-NH2-Bn-NOTA)
S-2-(4-isothiocyanatobenzyl)-1,4,7-triazacyclononane-1,4,7-triacetic acid (or p-SCN-Bn-NOTA)
iv) 1,4,8,11-tetraazacyclododecane-1,4,8,11-tetraacetic acid (or TETA) and its derivatives,
v) 1,4,7,10-tetraazacyclotridecane-N,N',N'',N'''-tetracetic acid (or TITRA) and its derivatives,
vi) triethylenetetramine hexaacetic acid (or TTHA) and its derivatives,
vii) 1,4,7-triazacyclononane-1-glutaric acid-4,7-diacetic acid (or NODAGA) and its derivatives,
viii) 1,4,7-triazacyclononane-1-succinic acid-4,7-diacetic acid (or NODASA) and its derivatives.

According to one embodiment of the invention, DTPA or its derivatives (class i above) are selected to form a complex with a detectable element selected from indium and gallium isotopes, specifically $^{67}$Ga, $^{68}$Ga and $^{111}$In.

According to another embodiment of the invention, DOTA or its derivatives (class ii above) is selected to form a complex with a detectable or cytotoxic element selected from indium, gallium, copper, scandium, yttrium, lutetium, bismuth, and thorium isotope, specifically $^{111}$In, $^{67}$Ga, $^{68}$Ga, $^{64}$Cu, $^{44}$Sc, $^{90}$Y, $^{177}$Lu, $^{67}$Cu, $^{47}$Sc, $^{212}$Bi, $^{213}$Bi or $^{226}$Th.

The invention relates very specifically to a neurotensin analogue of one of the following formulas:

Ac-Lys$^6$(DTPA)-Pro$^7$-NMe-Arg$^8$-Arg$^9$-Pro$^{10}$-Tyr$^{11}$-Tle$^{12}$-Leu$^{13}$-OH

Ac-Lys$^6$(DOTA)-Pro$^7$-NMe-Arg$^8$-Arg$^9$-Pro$^{10}$-Tyr$^{11}$-Tle$^{12}$-Leu$^{13}$-OH

Ac-Lys$^6$(Ahx-DOTA)-Pro$^7$-NMe-Arg$^8$-Arg$^9$-Pro$^{10}$-Dmt$^{11}$-Tle$^{12}$-Leu$^{13}$-OH

Regardless of whether the compound of the present invention is used for treatment or diagnosis, it can be administered parenterally, intravenously, intraperitoneally, by intracavitary or intravesical instillation, intraarterially or intralesionally. It may be administered alone or with a pharmaceutically or physiologically acceptable carrier, excipient, or stabilizer, in liquid form.

The treatment and/or therapeutic use of the compound of the present invention can be used in conjunction with other treatment and/or therapeutic methods. Such other treatment and/or therapeutic methods include surgery, radiation, cryosurgery, thermotherapy, hormone treatment, chemotherapy, vaccines, other immunotherapies, and other treatments and/or therapeutic methods which are regularly described.

The compounds of the present invention may be used in combination with either conventional methods of treatments and/or therapy or may be used separately from conventional methods of treatments and/or therapy.

When the compounds of this invention are administered in combination therapies with other agents, they may be administered sequentially or concurrently to an individual. Alternatively, pharmaceutical compositions according to the present invention may be comprised of a combination of a compound of the present invention, as described herein, and another therapeutic or prophylactic agent known in the art.

Further aspects and advantages of this invention will be disclosed in the following figures and examples, which should be regarded as illustrative and not limiting the scope of this application.

EXAMPLES

In the following examples DTPA-NT-20.3, DOTA-NT-20.3 and DOTA-LB119 are neurotensin analogues according to the invention. Other neurotensin analogues are presented for comparison.

1. Synthesis of the DTPA- and DOTA-NT Analogues
1.1 Synthesis of the DTPA-NT Analogues DTPA-NT-VI, DTPA-NT-XI, DTPA-Ahx-NT-XII, DTPA-Ahx-NT-XIX are DTPA-NT(8-13) analogues, that were stabilized against enzymatic degradation at the bonds between Arg$^8$ and Arg$^9$, Pro$^{10}$ and Tyr$^{11}$ or Tyr$^{11}$ and Ile$^{12}$ by changes introduced in the peptide sequence (Table 1).

DTPA-NT-20.1, DTPA-NT-20.2 and DTPA-NT-20.3 are analogues of the 6-13 sequence of [Lys$^6$(DTPA)]-NT. The N terminal end was acetylated. In these analogues DTPA was coupled to the ε-NH$_2$ group of Lys.

All reagents used for the synthesis were obtained from Sigma-Aldrich (Saint Quentin Fallavier, France or Bornem, Belgium), Novabiochem (Läufelfingen, Switzerland), Bachem (Bubendorf, Switzerland) and RSP (Shirley, USA). The purity of the compounds was checked by HPLC on a Nucleosil C$_{18}$ (5 μm, 100 Å, Shandon, France) reverse phase column or on a Discovery®BIO SUPELCO Wide Pore (5 μm, 300 Å, Sigma-Aldrich) column with a gradient of A: water (0.05% TFA) and B: CH$_3$CN (0.05% TFA) at a flow rate of 1 mL/min on a Waters apparatus.

The NT(8-13), NT-VI, NT-XI, NT-XII and NT-XIX peptides (Table 1) were prepared by solid phase peptide synthesis as described in detail elsewhere (Bruehlmeier et al., Nucl. Med. Biol. (2002) 29, 321-327; Maes et al., J. Med. Chem. (2006) 49, 1833-1836; Bergmann et al., Nucl. Med. Biol. (2002) 29, 61-72). Tris-tBu-DTPA (3 eq.) (Achilefu et al., J. Org. Chem. (2000) 65, 1562-1565) was coupled to the resin-bound neurotensin analog in a mixture of DMF/CH$_2$Cl$_2$ using 2-1H(benzotriazol-1-yl)-1,1,3,3-tetramethyl-ureum tetrafluoroborate (TBTU), 1-hydroxybenzotriazole (HOBt) and diisopropylethylamine (DIPEA) during 4 h.

The acetylated NT(6-13) analogues were synthesized by NeoMPS (Strasbourg, France). DTPA was coupled to the lysine ε-NH$_2$ as already described (Janevik-Ivanovska et al., Bioconjug. Chem. (1997) 8, 526-533).

All DTPA-peptides were purified to at least 92% purity and identified by mass spectrometry (Table 1).

TABLE 1

Peptide sequence and analytical data

| Peptide | Sequence | % purity | M + H$^+$ MALDI-TOF | M + H calculated |
|---|---|---|---|---|
| NT(1-13) analogues | | | | |
| NT | pGlu-Leu-Tyr-Glu-Asn-Lys-Pro-Arg-Arg-Pro-Tyr-Ile-Leu-OH | | | |
| [Lys6(DTPA)]-NT | pGlu-Leu-Tyr-Glu-Asn-Lys(DTPA)-Pro-Arg-Arg-Pro-Tyr-Ile-Leu-OH | >95$^a$ | 2048.16$^a$ | 2048.32$^a$ |
| NT(8-13) analogues | | | | |
| NT(8-13) | H-Arg-Arg-Pro-Tyr-Ile-Leu-OH | | | |
| DTPA-NT(8-13) | DTPA-Arg-Arg-Pro-Tyr-Ile-Leu-OH | >96 | 1192.23 | 1192.62 |
| DTPA-NT-VI | DTPA-Lys-Ψ(CH$_2$-NH)-Arg-Pro-Tyr-Ile-Leu-OH | 95 | 1150.12 | 1150.65 |
| DTPA-NT-Xi | DTPA-Lys-Ψ(CH$_2$-NH)-Arg-Pro-Tyr-Tle-Leu-OH | 97 | 1150.33 | 1150.65 |
| DTPA-Ahx-NTXII | DTPA-Ahx-Arg-Me-Arg-Pro-Tyr-Tle-Leu-OH | 92 | 1319.11 | 1318.73 |
| DTPA-Ahx-NT-XIX | DTPA-Ahx-Arg-Me-Arg-Pro-Dmt-Tle-Leu-OH | 97 | 1346.50 | 1346.76 |
| NT(6-13) analogues | | | | |
| NT-20.1 | Ac-Lys-Pro-Arg-Arg-Pro-Tyr-Ile-Leu-OH | | | |
| NT-20.2 | Ac-Lys-Pro-Arg-Arg-Pro-Tyr-Tle-Leu-OH | | | |
| NT-20.3 | Ac-Lys-Pro-Me-Arg-Arg-Pro-Tyr-Tle-Leu-OH | | | |
| DTPA-NT-20.1 | Ac-Lys(DTPA)-Pro-Arg-Arg-Pro-Tyr-Ile-Leu-OH | >99 | 1459.78 | 1459.78 |
| DTPA-NT-20.2 | Ac-Lys(DTPA)-Pro-Arg-Arg-Pro-Tyr-Tle-Leu-OH | >97 | 1459.77 | 1459.78 |
| DTPA-NT-20.3 | Ac-Lys(DTPA)-Pro-Me-Arg-Arg-Pro-Tyr-Tle-Leu-OH | >99 | 1473.83 | 1473.80 |

TABLE 1-continued

Peptide sequence and analytical data

| Peptide | Sequence | % purity | M + H⁺ MALDI-TOF | M + H calculated |
|---|---|---|---|---|
| DOTA-NT-20.3 | Ac-Lys(DOTA)-Pro-Me-Arg-Arg-Pro-Tyr-Tle-Leu-OH | 98 | 1484.83 | 1484.85 |
| DOTA-LB119[b] | Ac-Lys(Ahx-DOTA)-Pro-Me-Arg-Arg-Pro-Dmt-Tle-Leu-OH | >95 | 1627.08 | 1626.98 |

[a]Results already described (Hillairet De Boisferon et al., *Bioconjug. Chem.* (2002) 13, 654-662).
[b]Ahx: 6-aminohexanoic acid.

The following peptides DTPA-NT-20.3, DOTA-NT-20.3, DOTA-LB119 are neurotensin analogues according to the invention.

1.2. Synthesis of the DOTA-NT Analogues

All reagents used for the synthesis were obtained from Sigma-Aldrich (Saint Quentin Fallavier, France or Bornem, Belgium), Macrocyclics (Dallas, USA), Novabiochem (Läufelfingen, Switzerland), Bachem (Bubendorf, Switzerland) and RSP (Shirley, USA). The purity of the compounds was checked by HPLC on a Nucleosil C18 (5 μm, 100 Å, Shandon, France) reverse phase column or on a Discovery®BIO SUPELCO Wide Pore (5 μm, 300 Å, Sigma-Aldrich) column with a gradient of A: water (0.05% TFA) and B: CH3CN (0.05% TFA) at a flow rate of 1.5 mL/min on a Waters apparatus.

The acetylated NT(6-13) analogue NT-20.3 (Ac-Lys-Pro-Me-Arg-Arg-Pro-Tyr-Tle-Leu-OH) was synthesized by NeoMPS (Strasbourg, France). 1,4,7,10-Tetraazacyclododecane-1,4,7-tris(acetic acid)-10-acetic acid mono(N-hydroxysuccinimidyl ester) (DOTA-NHS ester) (Macrocyclics, Dallas, Tex., USA) (5 eq.) was coupled to the lysine ε-NH2 of NT-20.3 (1 eq.) as described (1). This DOTA-NT20.3 was purified by C18 reverse phase chromatography (5 μm, 100 Å, Nucleosil, Shandon, France) using a linear 150-minute gradient (Flow: 2 mL/min, A: H2O/TFA (0.05%), B: acetonitrile/TFA(0.05%)) from 0% to 37% B. Coupling yield was approximately 85% for DOTA-NT-20.3.

DOTA-LB119 was obtained starting from Ac-Lys(Dde)-Pro-MeArg(Pbf)-Arg(Pbf)-Pro-Dmt(Trt)-Tle-Leu-OWang resin. After deprotection of the Dde protection using NH2OH.HCl/imidazole, (Brans et al., Chemical Biology & Drug Design, (2008) 72, 496-506). Fmoc-Ahx was coupled to the free ε-NH2 group of Lys (DIC/HOBt) followed by Fmoc deprotection and coupling of DOTA(OtBu)3 using HATU. The peptide was cleaved from the resin using TFA/H2O/thioanisole/phenol/ethanedithiol (82.5:5:5:5:2.5), and purified by HPLC.

All DOTA-peptides were purified to at least 95% purity and identified by mass spectrometry (Table 1).

2. Radiolabeling

The DTPA-NT analogues were labeled with indium-111 ($^{111}$InCl$_3$, 60 or 180 MBq, CIS bio International, France) in 100 mM acetate, 10 mM citrate, buffer pH 5 during 22 h at room temperature, then free DTPA groups were saturated with non-radioactive InCl$_3$ as already described (Raguin et al., *Angew. Chem. Int. Ed. Engl.* (2005) 44, 4058-4061). The DOTA-NT (1 nmol) analogues were labeled with indium-111 ($^{111}$InCl$_3$, 10-20 MBq, CIS bio International, France) in 270 mM acetate, 27 mM citrate, buffer pH 4.5 during 25 minutes at 95° C.

3. Determination of the NTS1 Binding Affinities and Internalization Studies.

3.1. Materials and Methods 3.1.1. Binding to HT29 Cell Membranes.

Cell membranes (60 μg protein), were incubated for 45 min at room temperature in 250 μL buffer (50 mM Tris HCl, 5 mM MgCl$_2$, 0.8 mM 1,10-phenanthroline, 0.2% BSA, pH 7.4), in the presence of 50 pM $^{125}$I-Tyr$^3$-neurotensin (Perkin-Elmer) and increasing concentrations of non-radioactive DTPA(In)-NT analogues. Membrane bound activity was recovered by filtration onto Whatman GF/B filters presoaked for 1 hour with polyethyleneimine (0.2% in water) and rinsed twice with buffer. Non-specific binding was evaluated in the presence of $10^{-6}$ M neurotensin. Radioactivity was counted and results were analyzed with GraphPad Prism® (GraphPad Software, Inc. San Diego, Calif.). All experiments were performed three times in triplicate.

3.1.2. Binding to Living HT29 Cells and Internalization

IC50 for the binding to living HT29 cells were determined from competition experiments between [Lys$^6$(DTPA($^{111}$In))]-NT and the peptides without DTPA or DTPA(In)-Ahx-NT-XIX. For the other DTPA-peptides IC50 was evaluated using the labeled DTPA($^{111}$In)-peptide and increasing concentrations of the corresponding non radioactive DTPA(In)-peptide. IC 50 of non radioactive DOTA(metal)-peptide complex (DOTA(Me)-peptide with Me:In; Y or Lu) was determined using trace amounts of $^{125}$I-NT and increasing concentrations of the DOTA(Me)-peptide. For non radioactive metal chelation the DOTA-peptides (150 nmol in 150 μL water) were incubated (25 min 95° C.) with a solution of non radioactive InCl$_3$, YCl$_3$, or GaCl$_3$ (1.5 mmol in 150 μL acetate 100 mM, citrate 10 mM, buffer).

Cells were rinsed by 500 μL DMEM, 0.2% BSA, and incubated with the labeled analogue (DTPA($^{111}$In)-NT analogue 150 pM or $^{125}$I-NT 40 pM, 300 μL DMEM, 0.2% BSA, 0.8 mM 1,10-phenanthroline, 60 min, 37° C.) in the presence of increasing concentrations of non-radioactive DTPA(In)-NT analogue or DOTA(Me)-peptide. After washing the wells twice with ice-cold DMEM 0.2% BSA, cells were lysed in 500 μL 0.1N NaOH and radioactivity was counted. Non-specific binding was evaluated in the presence of $10^{-6}$ M neurotensin. Competition curves were analyzed with the "Equilibrium Expert" software (Raguin et al., *Anal. Biochem.* (2002) 310, 1-14). All experiments were performed three times in triplicate.

Incubation for internalization studies was performed with $0.15 \times 10^{-9}$ M DTPA($^{111}$In)-NT analogue or $0.5 \times 10^{-9}$M DOTA($^{111}$In)-NT20.3 or DOTA($^{111}$In)-LB119 as above except for the use of twelve-well plates (600 μL). At selected times the total binding was evaluated as above. To determine the amount of internalized radioactivity wells were incubated in DMEM/0.2% BSA, pH 2.0 for 15 min at 4° C., to dissociate the surface-bound ligand. Internalized activity was then counted after washing. Non-specific binding and internalization was evaluated in the presence of $10^{-6}$ M neurotensin. Results are expressed as the ratio between internalized and specifically bound radioactivity.

3.2. Binding and Internalization Results $K_i$ values for binding to HT29 cell membranes and IC50 for binding to cells were used to evaluate affinity (Table 2). $K_i$ values for binding to HT29 membranes were, for most peptides, about 10 times lower than the IC50 for the binding to HT29 cells. This can be attributed to the decreased affinity for binding to the NTS1 induced by sodium (Kitabgi et al., *Peptides* (2006) 27, 2461-2468) and to the effects of internalization and externalization of radioactivity in cells.

DTPA(In) coupled to the $NH_2$-α of NT(8-13) induced an important decrease in the affinity for membranes and for cells (by a factor of 31 and 32 respectively) as compared to NT(8-13). This loss of affinity is less important when the distance between the receptor-binding (8-13) sequence and DTPA is larger. When coupling DTPA to the ε-$NH_2$ of $Lys^6$ of NT, the affinity loss is only a factor of 6 for membranes and of 10 for cells. Similarly the affinity loss in DTPA(In)-NT-20.1 is only a factor of 9 and 8 as compared to NT-20.1. As a result, the affinity of DTPA(In)-NT-20.1 was two fold higher than that of DTPA(In)-NT(8-13), even though NT(8-13) displayed an affinity slightly higher than that of NT-20.1.

TABLE 2

Affinity of peptides for binding to HT29 cells or cell membranes.

| Peptide | $K_i$ (nM) membranes | IC50 (nM) cells |
|---|---|---|
| NT | 0.28 ± 0.05 | 1.67 ± 0.40 |
| [$Lys^6$(DTPA(In))]-NT | 1.77 ± 0.39 | 17.3 ± 4.3 |
| NT(8-13) | 0.044 ± 0.009 | 0.68 ± 0.04 |
| DTPA(In)-NT(8-13) | 1.36 ± 0.39 | 21.7 ± 5.1 |
| DTPA(In)-NT-VI | 3.20 ± 0.81 | 14.7 ± 1.6 |
| DTPA(In)-NT-XI | 8.11 ± 1.03 | 101 ± 17 |
| DTPA(In)-Ahx-NTXII | 5.26 ± 1.24 | 132 ± 44 |
| DTPA(In)-Ahx-NT-XIX | 67 ± 11 | 626 ± 30 |
| NT-20.1 | 0.072 ± 0.019 | 0.82 ± 0.08 |
| NT-20.2 | 0.26 ± 0.07 | 2.46 ± 0.79 |
| NT-20.3 | 0.16 ± 0.03 | 2.20 ± 0.31 |
| DTPA(In)-NT-20.1 | 0.66 ± 0.1 | 6.73 ± 0.31 |
| DTPA(In)-NT-20.2 | 1.55 ± 0.42 | 41.2 ± 6.2 |
| DTPA(In)-NT-20.3 | 2.24 ± 0.21 | 15.9 ± 1.7 |
| DOTA(In)-NT-20.3 | ND | 14.9 ± 1.1 |
| DOTA(Ga)-NT-20.3 | ND | 13.9 ± 2.2 |
| DOTA(Y)-NT-20.3 | ND | 7.0 ± 0.7 |
| DOTA(In)LB119 | ND | 14.1 ± 0.7 |
| DOTA(Ga)LB119 | ND | 7.5 ± 0.7 |
| DOTA(Y)LB119 | ND | 9.9 ± 0.4 |

N-methylation of the $Arg^8$-$Arg^9$ bond and introduction of an aminohexanoic acid spacer between DTPA and the 8-13 receptor binding sequence did not improve the affinity of DTPA(In)-Ahx-NT-XII as compared to DTPA(In)-NT-XI. Replacement of $Tyr^{11}$ by 2',6'-dimethyltyrosine in DTPA(In)-Ahx-NT-XIX led to an additional loss of affinity.

Introduction of a $Tle^{12}$ in the NT(6-13) series induced a decrease in affinity similar to that observed in the DTPA(In)-NT(8-13) series. N-methylation of the $Pro^7$-$Arg^8$ bond had little effect on affinity. Because the affinity of NT-20.1 was higher than that of NT, DTPA coupling and sequence modifications to the doubly-stabilized DTPA(In)-NT-20.3, the only peptide of this series which is a neurotensin analogue according to the invention, resulted in a high affinity, for membranes and for living cells, similar to those of the reference peptide [$Lys^6$(DTPA(In))]-NT.

The DTPA(In)-peptides exhibiting the highest affinities, [$Lys^6$(DTPA(In))]-NT, DTPA(In)-NT-VI, DTPA(In)-NT-XI, DTPA(In)-NT-20.1, DTPA(In)-NT-20.2, DTPA(In)-NT-20.3, were further evaluated for stability and tumor targeting in vivo.

DOTA coupling had similar effects as DTPA since DOTA(In)-NT20.3 affinity to cells was similar to that of its DTPA(In)-counterpart. The substitution of Tyr by Dmt and introduction of an aminohexanoic acid spacer between DOTA and the ε-NH2 of $Lys_6$ in DOTA(In)-LB119 had no effect on affinity.

The gallium chelate of DOTA-NT-20.3 exhibited an affinity similar to that of the indium complex, in opposition to the affinity increase of the yttrium chelate. Unexpectedly the gallium complexe of DOTA-LB119 displayed an affinity increase similar to that of the yttrium complexe as compared to the indium one. The high affinities observed for the complexes of DOTA-NT20.3 and DOTA-LB-119 with gallium and yttrium suggest that these peptides are suitable for in vivo targeting of their radioisotopes.

DTPA($^{111}$In)-NT-20.3 and DOTA($^{111}$In)-NT-20.3 internalized rapidly in HT29 cells, reaching a 86±3% and a 84±1% internalization plateau with a $t_{1/2}$ of 2.1±0.4 and 4.8±0.1 min respectively (Table 3). DOTA($^{111}$In)-LB119 internalization $t_{1/2}$ was significantly lower.

TABLE 3

Peptide internalization in HT29 cells

| Peptide | $t_{1/2}$ (min) | Plateau (%) |
|---|---|---|
| [$Lys^6$(DTPA($^{111}$In))]-NT | 4.2 ± 1.1 | 88 ± 6 |
| DTPA($^{111}$In)-NT-VI | 3.8 ± 1.2 | 82 ± 6 |
| DTPA($^{111}$In)-NT-20.3 | 2.1 ± 0.4 | 86 ± 3 |
| DOTA($^{111}$In)-NT-20.3 | 4.8 ± 0.1 | 84 ± 1 |
| DOTA($^{111}$In)-LB119 | 19.3 ± 0.7 | 93 ± 1 |

4. Metabolic Stability 4.1. In Human Serum

Serum from healthy donors (100 μL) was incubated with the DTPA($^{111}$In) analogues (2 pmol, 37° C.). Samples were collected at different time points and proteins were precipitated with methanol and filtered. Then methanol was evaporated under vacuum and the sample was analyzed by $C_{18}$ RP-HPLC. Detection was performed with a radioactivity detector (HERM LB 500, Berthold, France). Elution was performed using, after 5 min 0% B, a linear 10-minute gradient from 0% to 35% B and a linear 25-minute gradient from 35% to 50%, flow rate 1.5 mL/min. The sample was also co-injected with the radioactive control to identify the peak corresponding to intact peptide.

Figure 2:
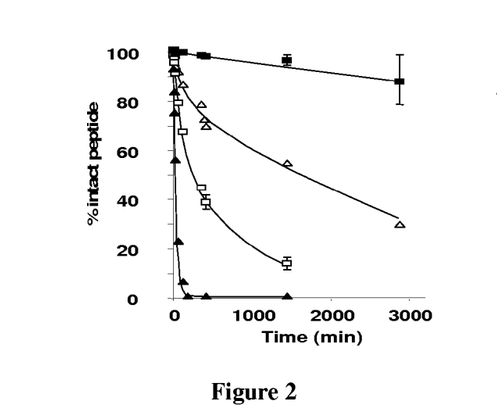
FIG. 2: Degradation kinetics of DTPA($^{111}$In)-peptides in human serum. Peptides (2 pmol) were incubated with human serum (100 μL) at 37° C.: [Lys$^6$(DTPA(In))]-NT open triangle, DTPA(In)-NT-20.1 black triangle, DTPA(In)-NT-20.2 open square, DTPA(In)-NT-20.3 black square (mean±sem, three independent experiments).
Figure 3:
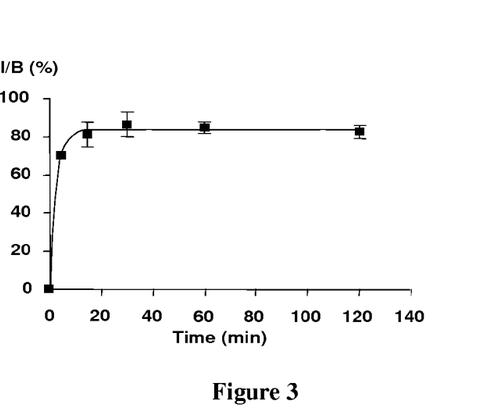
FIG. 3: Internalisation of DTPA($^{111}$In)-NT20.3 in HT29 cells. Results are expressed as the ratio between internalized and specifically bound radioactivity (I/B, mean±sem, 3 experiments in triplicate).

The in vitro stability in human serum was evaluated for $^{111}$In-labeled DTPA-NT(6-13) analogues and for the reference peptide (FIG. 2, Table 4). In agreement with the in vivo results, the unprotected peptide DTPA($^{111}$In)-NT-20.1 was very rapidly degraded and DTPA($^{111}$In)-NT-20.3, a neurotensin analogue according to the invention, was more stable than DTPA($^{111}$In)-NT-20.2. These results confirmed the stabilizing effect of the two modifications. By contrast to the rapid degradation observed in vivo, the unprotected [$Lys^6$(DTPA($^{111}$In))]-NT displayed an in vitro stability higher than that of the mono-stabilized DTPA($^{111}$In)-NT-20.2. These results point out the discrepancies that could occur between in vitro and in vivo degradation even when low tracer amounts are used in vitro in order to avoid saturation of peptidases (Garcia-Garayoa et al., *Nucl. Med. Biol.* (2001) 28, 75-84).

4.2. In Vivo Stability

Female BALB/c mice were injected in the tail vein with $^{111}$In-labeled DTPA-NT analogues (25 pmol) or with $^{111}$In-labeled DOTA-NT analogues (50 pmol). The mice were sacrificed 15 minutes after injection. Plasma and urine samples (50 µL) were added to 200 µL methanol and treated as above except for the DOTA-peptides for which elution was performed using, after 5 min 0% B, a linear 15-minute gradient from 0% to 35% B and a linear 25-minute gradient from 35% to 50%, flow rate 1.5 mL/min.

TABLE 4

In vitro and in vivo stability of DTPA-peptides.

| Peptide | In vitro stability ($t_{1/2}$ h)[a] | In vivo stability (% intact peptide)[b] | |
|---|---|---|---|
| | | in plasma | in urine |
| [Lys$^6$(DTPA(In))]-NT | 25 ± 2 | 4 (3-5) | 0 |
| DTPA(In)-NT-VI | ND | 10 (5-15) | 14.5 (15-14) |
| DTPA(In)-NT-XI | ND | 47 (40-53) | 21 (26-16) |
| DTPA(In)-NT-20.1 | 0.4 ± 0.02 | 0.8 (0.8-0.8) | 0 |
| DTPA(In)-NT-20.2 | 4.4 ± 0.6 | 10 (6-14) | 0 |
| DTPA(In)-NT-20.3 | 257 ± 71 | 26.5 (26-27) | 24 (23-31-19) |

[a]In vitro stability is expressed as the degradation half-life in human serum at 37° C.
[b]In vivo stability is expressed as the % intact peptide (mean (individual values)) recovered in plasma or urine 15 min after tracer injection

TABLE 5

In vivo stability of DOTA-peptides.

| Peptide | In vivo stability (% intact peptide)[a] | |
|---|---|---|
| | in plasma | in urine |
| DOTA(In)-NT-20.3 | 21 ± 2 | 26 ± 6 |
| DOTA(In)-LB119 | 28 ± 3 | ND |

[a]In vivo stability is expressed as the % of radioactivity associated to intact peptide (mean ± sem) recovered in plasma 15 min after tracer injection (n = 3-4)

Figure 1:
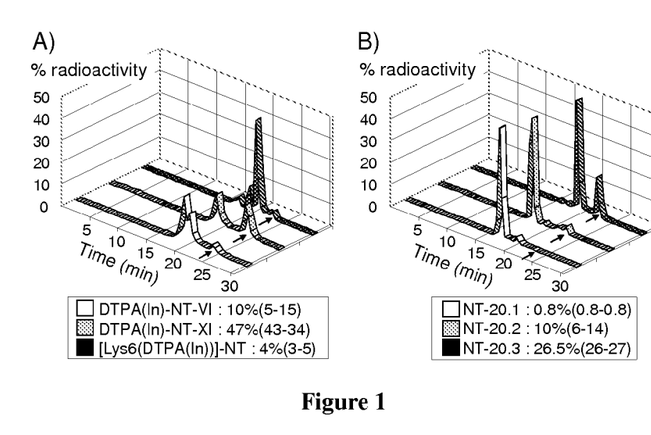
FIG. 1: In vivo serum stability of DTPA($^{111}$In)-peptides: representative C18 HPLC chromatograms of plasma samples collected 15 minutes post-injection to mice. A: reference peptide and NT(8-13) analogues, B: NT(6-13) analogues. Arrows show the intact peptide retention time. Mean percent radioactivity associated to intact peptide and individual values (between brackets) are indicated.

The fraction of radioactivity associated to the intact $^{111}$In-labeled peptide in serum and in urine determined 15 minutes after iv injection to BALB/c mice are presented in Table 4 and 5. Metabolites eluted by $C_{18}$ RP-HPLC chromatography at shorter retention times than the radioactive full-length peptide. The non-stabilized peptides [Lys$^6$(DTPA(In))]-NT and DTPA($^{111}$In)-NT-20.1 were rapidly catabolized (FIG. 1, Table 4). Protection of Arg$^8$-Arg$^9$ (DTPA($^{111}$In)-NT-VI) or Tyr$^{11}$-Ile$^{12}$ (DTPA($^{111}$In)-NT-20.2) bonds improved the stability. Peptides with two or three sequence modifications were much more resistant (Table 4-5). Higher amounts of intact tracer were recovered in serum and about 20% of the intact peptide was excreted in urine.

6. Biodistribution and Imaging Studies

6.1 Biodistribution and Imaging Studies: Materials and Methods

All in vivo experiments were performed in compliance with the French guidelines for experimental animal studies and fulfill the UKCCCR guidelines for the welfare of animals in experimental neoplasia.

HT29 cells ($6.7 \times 10^5$ cells) were injected subcutaneously in the flank of 6-8 week old athymic nu/nu mice, (Harlan, France). Two weeks later mice were i.v. injected with $^{111}$In-labeled DTPA-NT analogues (20-50 pmol in 100 µL PBS) or DOTA-analogues (40-65 pmol, 0.5-0.7 MBq, except for mice dissected 49 h post injection: 500-900 pmol, 7-12 MBq) and sacrificed at different times. Blood, organs and tumors were collected, weighted and radioactivity was counted. Injected activity was corrected for losses by subtraction of non-injected and subcutaneously injected material (remaining in the animal tail). In blocked experiments each mouse received a co-injection of the labeled peptide and of its unlabeled counterpart (60 nmol of NT for [Lys$^6$(DTPA(In))]-NT or 180 nmol of NT-20.3 for DTPA-NT-20.3, DOTA-NT-20.3 and of LB119 (Ac-Lys(Ahx)-Pro-Me-Arg-Arg-Pro-Dmt-Tle-Leu-OH) for DOTA-LB119). Statistical analysis of differences in the tissue uptake values was performed using unpaired t test for comparison between two groups, or ANOVA variance analysis followed by Newman-Keuls' test for multiple comparisons. Differences of $p < 0.05$ were considered significant.

Scintigraphic imaging was performed under pentobarbital anesthesia after iv injection of the $^{111}$In-labeled analogue (DTPA($^{111}$In)-NT-20.3: 30-50 pmol, 9-13 MBq, DOTA-NT analogues: 500-900 pmol, 7-12 MBq) using a dedicated small animal Gamma Imager-S/CT system (Biospace Mesures) equipped with parallel collimators (matrix 128×128, with 15% energy windows centered on both indium-111 peaks at 171 and 245 KeV). SPECT images (1 h acquisition) were obtained after volume reconstruction using an iterative algorithm. Tumor to background activity (evaluated in a ROI symmetrical to that of the tumor, counts per mm$^2$) ratio was evaluated on planar images. Radioactivity excretion in urine was determined from activity at 1 h post-injection in the bladder.

6.2 Results of Biodistribution and Imaging Studies of the DTPA-NT Series

The results of biodistribution studies of the DTPA-NT analogues, at 1 h and 3 h post-injection, performed in female nude mice grafted with HT29 cells are presented in tables 6 and 7. Biodistribution results of DTPA($^{111}$In)-NT-20.3 in female nude mice and in male nude mice from 1 h to 100 h after injection are presented in table 8 and table 9 respectively. They are expressed as the percentage of injected dose per gram of tissue (% ID/g).

TABLE 6

Tissue distributions of [Lys$^6$(DTPA($^{111}$In))]-NT and the DTPA($^{111}$In)-NT(8-13) analogues in female nude mice grafted with HT29 cells.

|  | [Lys6(DTPA($^{111}$In))]-NT | | | DTPA($^{111}$In)-NT-VI | DTPA($^{111}$In)-NT-XI |
|---|---|---|---|---|---|
|  | 1 h<br>n = 6 | 3 h<br>n = 9 | 3 h blocked[b]<br>n = 8 | 1 h<br>n = 3 | 1 h<br>n = 3 |
| Uptake (% ID/g)[a] | | | | | |
| Blood | 0.63 ± 0.12 | 0.06 ± 0.01 | 0.04 ± 0.01 | 0.24 ± 0.13 | 0.28 ± 0.02 |
| Lungs | 0.44 ± 0.06 | 0.07 ± 0.01 | 0.07 ± 0.01 | 0.21 ± 0.06 | 0.37 ± 0.02 |
| Liver | 0.22 ± 0.03 | 0.16 ± 0.07 | 0.09 ± 0.01 | 0.14 ± 0.06 | 0.19 ± 0.02 |
| Spleen | 0.19 ± 0.02 | 0.07 ± 0.01 | 0.45 ± 0.37 | 0.10 ± 0.02 | 0.18 ± 0.01 |
| Stomach[c] | 2.46 ± 2.01 | 0.26 ± 0.15 | 0.15 ± 0.09 | 0.06 ± 0.02 | 0.14 ± 0.02 |
| Small intestine[c] | 0.69 ± 0.09 | 0.59 ± 0.30 | 0.20 ± 0.09 | 0.28 ± 0.05 | 0.38 ± 0.07 |
| Large intestine[c] | 0.16 ± 0.02 | 0.71 ± 0.16 | 1.05 ± 0.47 | 0.17 ± 0.04 | 0.19 ± 0.04 |
| Muscle | 0.14 ± 0.03 | 0.03 ± 0.01 | 0.03 ± 0.01 | 0.11 ± 0.04 | 0.16 ± 0.08 |
| Bone | 0.13 ± 0.03 | 0.06 ± 0.01 | 0.03 ± 0.01 | 0.17 ± 0.05 | 0.13 ± 0.03 |
| Tumor | 1.02 ± 0.26 | 0.71 ± 0.18 | 0.22 ± 0.02 | 0.62 ± 0.06 | 0.52 ± 0.23 |
| Kidney | 12.50 ± 1.63 | 9.28 ± 0.73 | 7.18 ± 0.48 | 2.80 ± 0.37 | 3.90 ± 0.59 |
| Tumor(T)/organ | | | | | |
| T/Blood | 3.3 ± 2.1 | 10.9 ± 1.7 | 5.7 ± 0.5 | 4.9 ± 2.5 | 2.0 ± 0.9 |
| T/Liver | 5.8 ± 2.3 | 9.3 ± 0.8 | 2.8 ± 0.6 | 6.2 ± 2.3 | 3.0 ± 1.4 |
| T/Muscle | 10.4 ± 4.8 | 33.1 ± 4.1 | 8.9 ± 1.3 | 9.6 ± 5.6 | 3.4 ± 1.6 |
| T/Kidney | 0.08 ± 0.02 | 0.11 ± 0.01 | 0.03 ± 0.01 | 0.20 ± 0.04 | 0.16 ± 0.07 |

[a]Uptake is expressed as the percentage of injected dose per gram of tissue (% ID/g).
[b]Blocked animals received a co-injection of the labeled peptide with neurotensin (60 nmol).
[c]Organ with its content.

TABLE 7

Tissue distributions of the DTPA($^{111}$In)-NT(6-13) analogues in female nude mice grafted with HT29 cells.

|  | DTPA($^{111}$In)-NT-20.1 | | DTPA($^{111}$In)-NT-20.2 | | DTPA($^{111}$In)-NT-20.3 | | |
|---|---|---|---|---|---|---|---|
| Uptake (% ID/g)[a] | 1 h<br>n = 3 | 3 h<br>n = 6 | 1 h<br>n = 5 | 3 h<br>n = 5 | 1 h<br>n = 6 | 3 h<br>n = 15 | 3 h blocked[b]<br>n = 4 |
| Blood | 0.19 ± 0.03 | 0.03 ± 0.00 | 0.31 ± 0.06 | 0.02 ± 0.01 | 0.70 ± 0.09 | 0.04 ± 0.01 | 0.04 ± 0.01 |
| Lungs | 0.17 ± 0.01 | 0.04 ± 0.01 | 0.30 ± 0.04 | 0.10 ± 0.04 | 0.73 ± 0.04 | 0.17 ± 0.03 | 0.12 ± 0.01 |
| Liver | 0.11 ± 0.01 | 0.06 ± 0.01 | 0.14 ± 0.01 | 0.07 ± 0.01 | 0.39 ± 0.04 | 0.17 ± 0.05 | 0.08 ± 0.01 |
| Spleen | 0.08 ± 0.01 | 0.05 ± 0.01 | 0.12 ± 0.01 | 0.06 ± 0.01 | 0.31 ± 0.01 | 0.11 ± 0.01 | 0.09 ± 0.01 |
| Stomach (with content) | 0.13 ± 0.04 | 0.02 ± 0.01 | 0.42 ± 0.17 | 0.04 ± 0.01 | 0.66 ± 0.19 | 0.17 ± 0.04 | 0.14 ± 0.04 |
| Small intestine (with content) | 0.53 ± 0.20 | 0.18 ± 0.04 | 1.07 ± 0.44 | 0.16 ± 0.02 | 1.90 ± 0.22 | 1.30 ± 0.46 | 0.18 ± 0.05 |
| Large intestine (with content) | 0.09 ± 0.01 | 1.65 ± 0.99 | 0.11 ± 0.02 | 0.46 ± 0.09 | 0.42 ± 0.05 | 1.03 ± 0.14 | 0.15 ± 0.04 |
| Stomach (without content) | ND | ND | ND | ND | ND | 0.21 ± 0.03 | 0.09 ± 0.02 |
| Small intestine (without content) | ND | ND | ND | ND | ND | 0.78 ± 0.10 | 0.10 ± 0.03 |
| Large intestine (without content) | ND | ND | ND | ND | ND | 0.45 ± 0.04 | 0.09 ± 0.01 |
| Muscle | 0.07 ± 0.01 | 0.01 ± 0.01 | 0.07 ± 0.01 | 0.01 ± 0.01 | 0.16 ± 0.01 | 0.03 ± 0.01 | 0.04 ± 0.01 |
| Bone | 0.07 ± 0.01 | 0.03 ± 0.01 | 0.43 ± 0.22 | 0.03 ± 0.01 | 0.22 ± 0.05 | 0.11 ± 0.02 | 0.28 ± 0.11 |
| Tumor | 0.46 ± 0.06 | 0.49 ± 0.12 | 0.93 ± 0.32 | 0.46 ± 0.09 | 3.27 ± 0.21 | 2.38 ± 0.21 | 0.14 ± 0.03 |
| Kidney | 1.44 ± 0.25 | 1.36 ± 0.10 | 2.55 ± 0.24 | 1.97 ± 0.26 | 7.49 ± 0.54 | 4.85 ± 0.25 | 4.81 ± 0.63 |
| Tumor(T)/organ | | | | | | | |
| T/Blood | 2.5 ± 0.3 | 18.8 ± 4.7 | 4.6 ± 2.8 | 19.4 ± 3.7 | 5.6 ± 1.5 | 60.5 ± 6.8 | 3.7 ± 0.8 |
| T/Liver | 4.3 ± 0.4 | 8.5 ± 1.7 | 6.6 ± 2.1 | 6.5 ± 0.9 | 8.8 ± 0.6 | 19.1 ± 1.5 | 1.7 ± 0.2 |
| T/Muscle | 7.1 ± 1.9 | 35.6 ± 8.3 | 14.8 ± 6.7 | 34.0 ± 8.0 | 20.8 ± 1.4 | 91.6 ± 8.6 | 4.2 ± 1.0 |
| T/Pancreas | ND | ND | ND | ND | 17.5 ± 0.8 | 68.2 ± 6.5 | ND |
| T/Kidney | 0.32 ± 0.02 | 0.37 ± 0.04 | 0.35 ± 0.08 | 0.23 ± 0.01 | 0.44 ± 0.03 | 0.49 ± 0.04 | 0.03 ± 0.01 |

[a]Uptake is expressed as the percentage of injected dose per gram of tissue (% ID/g).
[b]Blocked animals received a co-injection of the labeled peptide with NT-20.3 (180 nmol).

DTPA($^{111}$In)-NT-20.3, which is in the DTPA-neurotensin series the only neurotensin analogue according to the present invention, displayed the highest tumor uptake as compared to other DTPA-NT analogues, about 3 fold higher than that of [Lys$^6$(DTPA($^{111}$In))]-NT at 1 h (3.3±0.2 vs 1.0±0.3% ID/g, P<0.001) and at 3 h (2.4±0.2 vs 0.7±0.2% ID/g, P<0.001). Radioactivity uptake of other peptides in tumor was much lower. Particularly, DTPA($^{111}$In)-NT-20.2 with only one sequence modification displayed low tumor uptake though the chelating agent was separated from Aa8 by a chain of 11 consecutive bonds.

The difference observed between tumor retention at 1 h and 3 h post-injection for DTPA($^{111}$In)-NT-20.3 was not statistically significant, indicating a slow wash out of radioactivity from the tumor, confirmed by the 0.33±0.04% ID/g tumor uptake observed 100 h post-injection (Table 6).

Tumor uptake of [Lys$^6$(DTPA($^{111}$In))]-NT or DTPA($^{111}$In)-NT-20.3 was receptor mediated since it was significantly reduced by co-injection of their unlabeled counterpart (78% reduction, P=0.02 and 94% reduction, P<0.0001 respectively).

Radioactivity in blood at 1 h post-injection was significantly higher for DTPA($^{111}$In)-NT-20.3 and [Lys$^6$(DTPA($^{111}$In))]-NT than for other peptides. It decreased rapidly with time for both peptides. Radioactivity excretion in urine was fast and amounted 69±4% of the injected dose 1 h after injection for DTPA($^{111}$In)-NT-20.3. Low activity accretion was observed in normal tissues for all peptides except in kidneys and, particularly for DTPA($^{111}$In)-NT-20.3, in gastrointestinal tract. Nevertheless, for DTPA($^{111}$In)-NT-20.3, high uptake ratios were obtained between tumor and stomach (7.2±1.7 at 1 h and 30±7 at 3 h), small intestine (1.8±0.2 and 3.5±0.6) and colon (8.3±0.8 and 3.0±0.5).

The basis of the gastrointestinal uptake of DTPA($^{111}$In)-NT-20.3 (Table 7) has been investigated. In contrast to colon uptake, which was significantly decreased by co-injection of the unlabeled analogue (P=0.004), stomach and small intestine uptakes were not significantly reduced by the co-injection, despite the expression of NTS1 in these organs. Most of the activity was associated to the content of the organs (stomach: 68±4%, small intestine: 59±6%, colon 73±6%) indicating an elimination by the gastrointestinal route. When organ content was removed, co-injection of DTPA($^{111}$In)-NT-20.3 with its unlabeled counterpart significantly decreased uptake at 3 h post-injection in stomach (P=0.04), in small intestine (P=0.001), and in colon (P=0.0002). These results suggest that some uptake in these tissues is receptor mediated, but most of the activity comes from gastrointestinal elimination.

Kidney uptake of DTPA(In)-NT-20.3 in female nude mice was significantly lower than that of [Lys$^6$(DTPA(In))]-NT and significantly higher than that of other tested peptides at 1 h and 3 h post-injection, with the exception of DTPA($^{111}$In)-NT-XI for which the difference was not significant. DTPA($^{111}$In)-NT-20.1 displayed the lowest renal accretion of the peptides tested in this DTPA series with 1.4±0.25% ID/g as soon as 1 h post injection.

Charge and charge distribution of radiolabeled peptides may produce various effects on renal uptake, but in general it is increased by positive charges (Akizawa et al., *Nucl. Med. Biol.* (2001) 28, 761-768; Froidevaux et al., *J. Nucl. Med.* (2005) 46, 887-895). One objective of the present invention was to lower kidney uptake as compared to the reference peptide. [Lys$^6$(DTPA($^{111}$In))]-NT may, after cleavage in the 1-6 N-terminal end, release labeled metabolites with a free positively charged α-NH$_2$, which could contribute to the high kidney uptake. To avoid the formation of these metabolites, the 1-6 N-terminal part of the molecule has been deleted and its N-terminal end has been acetylated to neutralize the positive charge. Cleavage of DTPA($^{111}$In)-NT-20.1 at the Arg$^8$-Arg$^9$ bond may produce labeled metabolites with only one positive charge (Arg$^8$).

The same is true for DTPA($^{111}$In)-NT-20.2, which also exhibits low renal uptake. In DTPA($^{111}$In)-NT-20.3, the Arg$^8$-Arg$^9$ bond is stabilized. Thus, a higher renal accumulation of radioactivity may be introduced by the release of metabolites with two positively charged -(-Arg-)-.

For DTPA($^{111}$In)-NT-20.3, tumor to normal tissues uptake ratios were elevated for most organs, particularly tumor/pancreas ratio was 17.5±0.8 and 68.2±6.5 at 1 and 3 h post injection respectively. They were markedly improved as compared to [Lys$^6$(DTPA($^{111}$In))]-NT particularly tumor/blood (60.5±6.8 vs 10.9±1.7 P<0.0001 at 3 h post-injection), tumor/liver (19.1±1.5 vs 9.3±0.8 P<0.0001) and tumor/muscle (91.6±8.6 vs 33.1±4.1 P<0.0001). Tumor to kidney uptake ratio was also improved about five fold (0.49±0.04 vs 0.11±0.01 P<0.0001, 3 h post-injection) as a result of higher radioactivity uptake in tumor and lower accretion in kidney for DTPA($^{111}$In)-NT-20.3.

DTPA($^{111}$In)-NT-20.3, as compared to DTPA-neurotensin conjugates previously described in the literature provided in male mice higher tumor uptake and/or higher tumor to kidneys uptake ratios at early times post injection.

Figure 4:
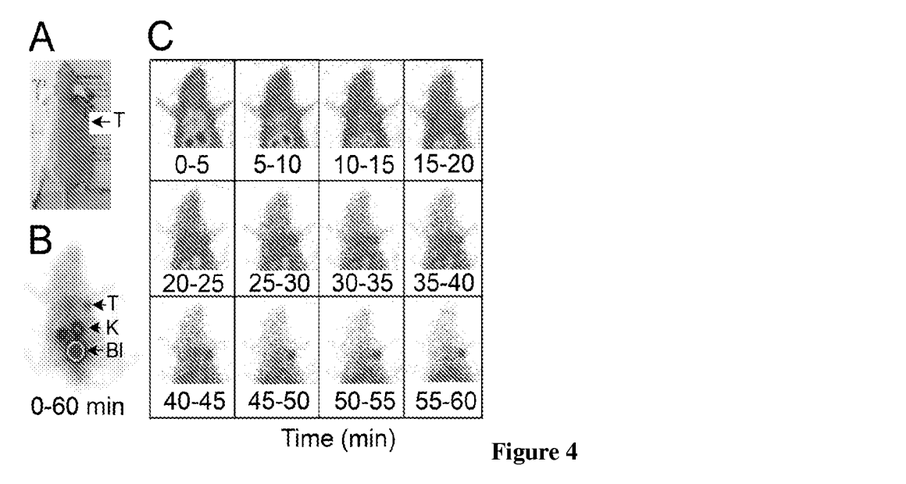
FIG. 4: DTPA($^{111}$In)-NT-20.3 planar images of a male nude mouse grafted with HT29 cells. A: photograph, B: planar anterior acquisition performed from 0 to 60 min post-injection under anaesthesia, C: dynamic series of images of 5 min each computed from the recorded scintigraphy data. B1: Bladder, K: Kidney, T: Tumor. Tumor weight: 240 mg.
Figure 5:
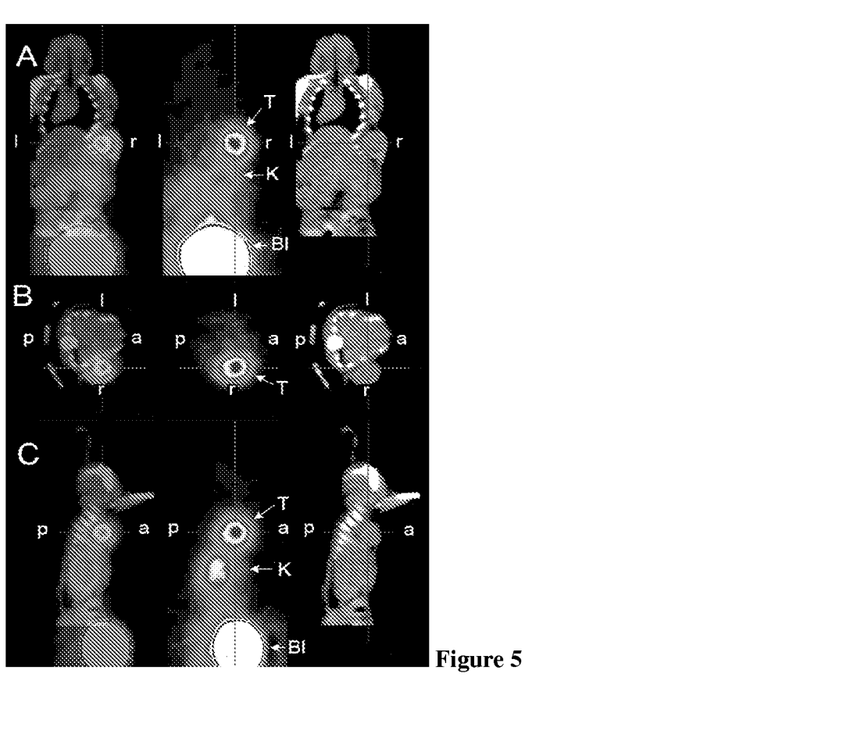
FIG. 5: SPECT/CT imaging of a male nude mice mouse grafted with HT29 cells in the right flank 2.5 h post-injection of DTPA($^{111}$In)-NT-20.3. Left: CT; center: SPECT, right: SPECT/CT fused images. Frames: A: coronal, B: axial, C: sagittal. Abbreviations as in FIG. 5 and r: right, l: left, a: anterior, p: posterior. Tumor weight: 498 mg.
Figure 6:
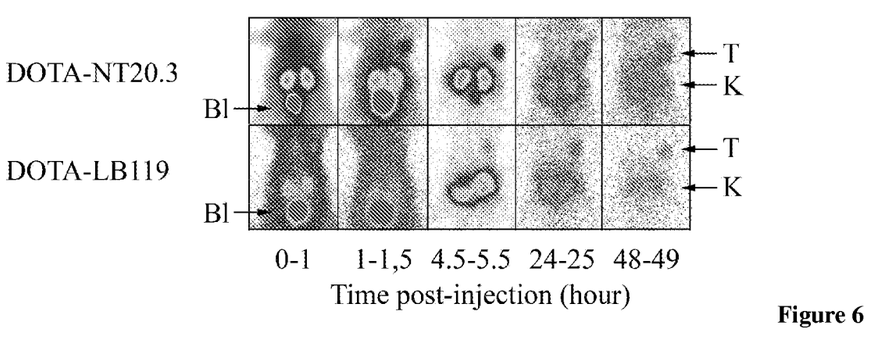
FIG. 6: DOTA($^{111}$In)-NT-20.3 and DOTA($^{111}$In)-LB119 planar images of male nude mice grafted with HT29 cells. Planar anterior acquisitions were performed from 0 to 1 h, 1 to 1.5 h, 4.5 to 5.5 h, 24 to 25 h and 48 to 49 h post-injection under anaesthesia. B1: Bladder, K: Kidney, T: Tumor.

Accumulation of DTPA($^{111}$In)-NT-20.3 was clearly observed in tumors in planar at early (FIG. 4) and late time points: 24, 48 and 100 h (not shown) post-injection and in tomographic images recorded in male mice (FIG. 5). Kidneys and bladder were the only other sites of activity accumulation. Tumor was detected as soon as 30 minutes post-injection on sequential 5 minutes acquisition images. Tumor-to-background ratio increased with time reaching 2.8±0.7 at 1 h and 4.5±1.0 at 24 h. At 24 h, the activity ratio between tumor and kidneys was 1.3±0.4 (tumor weight: 0.428±0.095 g).

6.3 Results of Biodistribution and Imaging Studies of the DOTA-NT Series

Biodistribution studies of neurotensin analogues according to the invention DOTA($^{111}$In)-NT-20.3 (Table 10), the DOTA analogue of DTPA($^{111}$In)-NT-20.3, and DOTA($^{111}$In)-LB119 (Table 11) were also performed at various time post injection in male nude mice. No significant difference was observed between tumor accretion of DTPA($^{111}$In)-NT-20.3 and of DOTA($^{111}$In)-NT-20.3 at any time post-injection (Anova and Student-Newman-Keuls Multiple Comparisons Test), indicating similar tumor targeting efficacy of these two peptides. In the DOTA-NT series at early times post-injection DOTA($^{111}$In)-NT-20.3 displayed an higher tumor uptake than DOTA($^{111}$In)-LB119 (1 h and 3 h P<0.05), but DOTA($^{111}$In)-LB119 tumor uptake decreased slowly with time and from 6 h to 24 h no significant difference was observed between these two peptides.

Renal accumulation of radioactivity was lower for DOTA($^{111}$In)-LB119 than for DOTA($^{111}$In)-NT20.3 at early times (P<0.05 from 1 to 6 h).

DOTA($^{111}$In)-NT-20.3 and DOTA($^{111}$In)LB119 as compared to DOTA neurotensin conjugates previously described in the literature, provided in male mice higher tumor uptake and/or higher tumor to normal tissue uptake ratios, particularly higher tumor to kidneys uptake ratios at early times post injection.

Figure 7:
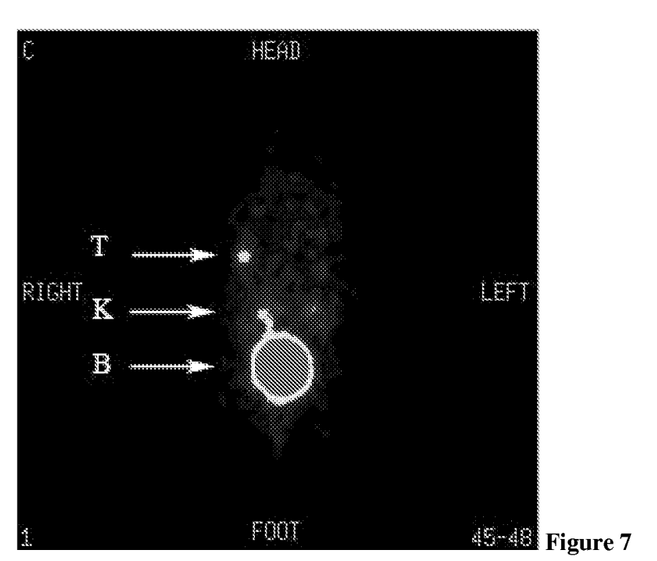
FIG. 7: TEP imaging of a male nude mouse, grafted with HT29 cells in the right flank, injected with DOTA($^{68}$Ga)-NT-20.3: coronal frame 47 minutes post injection, 10 min acquisition, tumor volume: 40 mm$^3$. B1: Bladder, K: Kidney, T: Tumor.

The efficacy of DOTA-NT-20.3 to target 68Ga in vivo to tumors expressing the NTSR1 receptor is shown by the TEP images recorded with this peptide (FIG. 7).

TABLE 8

Tissue distributions of DTPA($^{111}$In)-NT(20.3) in female nude mice grafted with HT29 cells from 1 h to 100 h.

| DTPA-NT-20.3 | 1 h | 3 h | 3 h blocked | 6 h | 24 h | 48 h | 100 h |
|---|---|---|---|---|---|---|---|
| Blood | 0.70 ± 0.09 | 0.043 ± 0.005 | 0.039 ± 0.002 | 0.028 ± 0.002 | 0.012 ± 0.001 | 0.0055 ± 0.0007 | 0.0029 ± 0.0005 |
| Lungs | 0.73 ± 0.04 | 0.17 ± 0.03 | 0.12 ± 0.01 | 0.10 ± 0.01 | 0.10 ± 0.01 | 0.048 ± 0.007 | 0.029 ± 0.002 |
| Liver | 0.39 ± 0.04 | 0.17 ± 0.06 | 0.079 ± 0.008 | 0.10 ± 0.01 | 0.081 ± 0.006 | 0.082 ± 0.008 | 0.050 ± 0.002 |
| Spleen | 0.31 ± 0.01 | 0.11 ± 0.01 | 0.092 ± 0.008 | 0.10 ± 0.01 | 0.12 ± 0.02 | 0.089 ± 0.014 | 0.055 ± 0.003 |
| Stomach | 0.66 ± 0.19 | 0.17 ± 0.04 | 0.14 ± 0.04 | 0.14 ± 0.03 | 0.10 ± 0.02 | 0.047 ± 0.005 | 0.022 ± 0.004 |
| Small intestine | 1.90 ± 0.22 | 1.30 ± 0.46 | 0.18 ± 0.05 | 0.42 ± 0.04 | 0.34 ± 0.04 | 0.23 ± 0.02 | 0.13 ± 0.01 |
| Large intestine | 0.42 ± 0.05 | 1.03 ± 0.14 | 0.15 ± 0.04 | 0.51 ± 0.19 | 0.36 ± 0.11 | 0.17 ± 0.03 | 0.23 ± 0.11 |
| Muscle | 0.16 ± 0.01 | 0.029 ± 0.004 | 0.042 ± 0.014 | 0.021 ± 0.002 | 0.020 ± 0.002 | 0.011 ± 0.003 | 0.0095 ± 0.0012 |
| Bone | 0.22 ± 0.05 | 0.11 ± 0.03 | 0.27 ± 0.11 | 0.068 ± 0.010 | 0.065 ± 0.013 | 0.054 ± 0.009 | 0.028 ± 0.004 |
| Tumor | 3.27 ± 0.21 | 2.38 ± 0.21 | 0.14 ± 0.03 | 1.63 ± 0.19 | 1.41 ± 0.21 | 0.55 ± 0.07 | 0.33 ± 0.04 |
| Kidney | 7.49 ± 0.54 | 4.85 ± 0.25 | 4.81 ± 0.63 | 3.62 ± 0.38 | 3.13 ± 0.43 | 1.80 ± 0.38 | 0.83 ± 0.05 |
| Pancreas | 0.19 ± 0.01 | 0.032 0.001 | | | | | |
| tumor weight | 0.48 ± 0.10 | 0.26 ± 0.046 | 0.0956 ± 0.028 | 0.49 ± 0.10 | 0.40 ± 0.041 | 0.1972 ± 0.02133 | 0.2327 ± 0.06114 |

TABLE 9

Tissue distributions of DTPA($^{111}$In)-NT(20.3) in male nude mice grafted with HT29 cells from 1 h to 100 h.

| DTPA-NT-20.3 | 1 h | 3 h | 6 h | 24 h | 48 h | 100 h |
|---|---|---|---|---|---|---|
| Blood | 0.13 ± 0.03 | 0.026 ± 0.004 | 0.023 ± 0.004 | 0.0076 ± 0.0008 | 0.0028 ± 0.0005 | 0.0017 ± 0.0006 |
| Lungs | 0.63 ± 0.35 | 0.11 ± 0.01 | 0.13 ± 0.04 | 0.044 ± 0.003 | 0.035 ± 0.003 | 0.18 ± 0.05 |
| Liver | 0.12 ± 0.01 | 0.093 ± 0.008 | 0.07 ± 0.01 | 0.048 ± 0.003 | 0.040 ± 0.002 | 0.063 ± 0.007 |
| Spleen | 0.13 ± 0.01 | 0.13 ± 0.02 | 0.10 ± 0.01 | 0.074 ± 0.004 | 0.064 ± 0.004 | 0.106 ± 0.017 |
| Stomach | 0.14 ± 0.03 | 0.076 ± 0.015 | 0.15 ± 0.05 | 0.27 ± 0.10 | 0.033 ± 0.008 | 0.018 ± 0.003 |
| Small intestine | 1.05 ± 0.37 | 0.47 ± 0.13 | 0.61 ± 0.09 | 0.38 ± 0.05 | 0.19 ± 0.01 | 0.098 ± 0.014 |
| Large intestine | 0.46 ± 0.15 | 0.23 ± 0.03 | 1.38 ± 0.23 | 0.81 ± 0.13 | 0.15 ± 0.03 | 0.037 ± 0.005 |
| Muscle | 0.52 ± 0.42 | 0.14 ± 0.09 | 0.023 ± 0.005 | 0.023 ± 0.007 | 0.016 ± 0.004 | 0.0083 ± 0.0027 |
| Bone | 0.20 ± 0.06 | 0.10 ± 0.020 | 0.083 ± 0.013 | 0.044 ± 0.003 | 0.027 ± 0.004 | 0.036 ± 0.005 |
| Tumor | 3.05 ± 0.36 | 1.99 ± 0.39 | 2.00 ± 0.24 | 0.86 ± 0.06 | 0.92 ± 0.13 | 0.38 ± 0.01 |
| Kidney | 7.79 ± 1.00 | 6.54 ± 1.69 | 2.84 ± 0.32 | 1.89 ± 0.33 | 1.50 ± 0.34 | 0.48 ± 0.08 |
| tumor weight | 0.26 ± 0.06 | 0.35 ± 0.04 | 0.40 ± 0.07 | 0.40 ± 0.042 | 0.65 ± 0.19 | 0.40 ± 0.07 |

TABLE 10

Tissue distributions of DOTA($^{111}$In)-NT(20.3) in male nude mice grafted with HT29 cells from 1 h to 49 h.

| DOTA-NT-20.3 | 1 h | 3 h | 3 h blocked | 4 h 30 | 6 h | 24 h | 49 h |
|---|---|---|---|---|---|---|---|
| Blood | 0.36 ± 0.06 | 0.033 ± 0.014 | 0.13 ± 0.01 | 0.015 ± 0.001 | 0.038 ± 0.012 | 0.0028 ± 0.0003 | 0.0028 ± 0.0004 |
| Lungs | 0.47 ± 0.04 | 0.14 ± 0.02 | 0.16 ± 0.01 | 0.12 ± 0.01 | 0.11 ± 0.01 | 0.061 ± 0.004 | 0.068 ± 0.011 |
| Liver | 0.21 ± 0.02 | 0.13 ± 0.02 | 0.12 ± 0.01 | 0.14 ± 0.01 | 0.12 ± 0.01 | 0.085 ± 0.002 | 0.072 ± 0.013 |
| Spleen | 0.19 ± 0.01 | 0.11 ± 0.01 | 0.10 ± 0.01 | 0.11 ± 0.01 | 0.11 ± 0.01 | 0.10 ± 0.01 | 0.16 ± 0.01 |
| Stomach | 0.13 ± 0.03 | 0.22 ± 0.12 | 0.081 ± 0.017 | 0.12 ± 0.03 | 0.092 ± 0.037 | 0.057 ± 0.013 | 0.020 ± 0.005 |
| Small intestine | 0.85 ± 0.10 | 0.52 ± 0.08 | 0.12 ± 0.02 | 0.58 ± 0.05 | 0.34 ± 0.06 | 0.32 ± 0.02 | 0.070 ± 0.003 |
| Large intestine | 0.39 ± 0.05 | 1.13 ± 0.30 | 0.18 ± 0.08 | 2.22 ± 0.96 | 1.47 ± 0.45 | 0.19 ± 0.02 | 0.058 ± 0.007 |
| Muscle | 0.10 ± 0.02 | 0.027 ± 0.008 | 0.053 ± 0.013 | 0.022 ± 0.005 | 0.042 ± 0.011 | 0.012 ± 0.001 | 0.008 ± 0.001 |
| Bone | 0.15 ± 0.02 | 0.10 ± 0.02 | 0.13 ± 0.03 | 0.056 ± 0.016 | 0.10 ± 0.01 | 0.030 ± 0.005 | 0.053 ± 0.002 |
| Tumor | 4.72 ± 0.76 | 2.48 ± 0.19 | 0.14 ± 0.02 | 2.40 ± 0.21 | 1.86 ± 0.20 | 1.26 ± 0.15 | 0.68 ± 0.09 |
| Kidney | 7.55 ± 0.85 | 4.89 ± 0.40 | 6.70 ± 0.23 | 4.07 ± 0.28 | 5.16 ± 0.47 | 2.50 ± 0.12 | 0.86 ± 0.08 |
| pancreas | 0.10 0.01 | 0.033 ± 0.010 | 0.028 ± 0.001 | | 0.030 ± 0.002 | | |
| tumor weight | 0.20 ± 0.03 | 0.185 ± 0.036 | 0.055 ± 0.010 | 0.14 ± 0.03 | 0.11 ± 0.03 | 0.21 ± 0.03 | 0.148 ± 0.042 |

TABLE 11

Tissue distributions of DOTA($^{111}$-In)-LB119 in male nude mice grafted with HT29 cells from 1 h to 49 h.

| DOTA-LB119 | 1 h | 3 h | 3 h blocked | 6 h | 24 h | 49 h |
|---|---|---|---|---|---|---|
| Blood | 0.38 ± 0.05 | 0.023 ± 0.002 | 0.042 ± 0.008 | 0.0045 ± 0.0002 | 0.0074 ± 0.0018 | 0.0021 ± 0.0003 |
| Lungs | 0.36 ± 0.03 | 0.11 ± 0.01 | 0.086 ± 0.010 | 0.086 ± 0.014 | 0.060 ± 0.013 | 0.041 ± 0.010 |
| Liver | 0.20 ± 0.01 | 0.15 ± 0.01 | 0.077 ± 0.005 | 0.14 ± 0.02 | 0.080 ± 0.005 | 0.089 ± 0.026 |
| Spleen | 0.15 ± 0.01 | 0.087 ± 0.011 | 0.077 ± 0.007 | 0.076 ± 0.009 | 0.064 ± 0.003 | 0.095 ± 0.027 |
| Stomach | 0.28 ± 0.08 | 0.16 ± 0.04 | 0.37 ± 0.21 | 0.52 ± 0.46 | 0.080 ± 0.013 | 0.024 ± 0.004 |
| Small intestine | 1.11 ± 0.10 | 0.67 ± 0.08 | 0.50 ± 0.19 | 0.69 ± 0.14 | 0.35 ± 0.05 | 0.084 ± 0.005 |

TABLE 11-continued

Tissue distributions of DOTA($^{111}$-In)-LB119 in male nude mice grafted with HT29 cells from 1 h to 49 h.

| DOTA-LB119 | 1 h | 3 h | 3 h blocked | 6 h | 24 h | 49 h |
|---|---|---|---|---|---|---|
| Large intestine | 0.44 ± 0.12 | 1.54 ± 0.53 | 0.17 ± 0.07 | 1.24 ± 0.81 | 0.16 ± 0.03 | 0.10 ± 0.01 |
| Muscle | 0.094 ± 0.013 | 0.021 ± 0.005 | 0.03 ± 0.01 | 0.049 ± 0.023 | 0.010 ± 0.003 | 0.015 ± 0.007 |
| Bone | 0.15 ± 0.03 | 0.047 ± 0.011 | 0.10 ± 0.05 | 0.068 ± 0.018 | 0.053 ± 0.010 | 0.049 ± 0.020 |
| Tumor | 1.83 ± 0.13 | 1.41 ± 0.05 | 0.12 ± 0.03 | 1.35 ± 0.18 | 0.98 ± 0.27 | 0.46 ± 0.06 |
| Kidney | 3.37 ± 0.20 | 2.40 ± 0.21 | 2.18 ± 0.19 | 2.15 ± 0.19 | 1.04 ± 0.07 | 0.64 ± 0.12 |
| Pancreas | 0.081 ± 0.008 | 0.022 ± 0.001 | 0.026 ± 0.006 | 0.018 ± 0.001 | 0.018 ± 0.001 | 0.013 ± 0.002 |
| tumor weight | 0.124 ± 0.019 | 0.306 ± 0.030 | 0.181 ± 0.018 | 0.121 ± 0.032 | 0.202 ± 0.095 | 0.195 ± 0.051 |

The invention claimed is:

1. A neurotensin analogue, or a salt thereof, of formula (I)

X-L-Aa8-Aa9-(L)Pro-Aa11-Aa12-(L)Leu    (I)

wherein
Aa8 is NMe-(L)Arg, Nme-(D)Arg, NMe-(L)Lys or NMe-(D)Lys, and
the sequence Aa9-(L)Pro-Aa11-Aa12-(L)Leu differs from (L)Arg-(L)Pro-(L)Tyr-(L)Ile-(L)Leu by at least one substitution in the amino acid sequence, the substitution(s) being selected from:
Aa9 is selected from the group consisting of (L)Lys, ψ(CH$_2$—NH)-(L)Arg, and ψ(CH$_2$—NH)-(L) Lys,
Aa11 is selected from the group consisting of (D)Tyr, (L)Dmt and (D)Dmt, and
Aa12 is selected from the group consisting of (L)Tle, (L)Leu and (L)Val,
X is a poly(aminocarboxylate) chelating moiety selected from the group consisting of:
i) diethylenetriamine pentaacetic acid (DTPA) and its derivatives,
ii) 1,4,7,10-tetraazacyclododecane-1,4,7,10-tetraacetic acid (DOTA) and its derivatives,
iii) 1,4,7-triazacyclononane-1,4,7-triacetic acid (NOTA) and its derivatives,
iv) 1,4,8,11-tetraazacyclododecane-1,4,8,11-tetraacetic acid (TETA) and its derivatives,
v) 1,4,7,10-tetraazacyclotridecane-N,N',N",N"'-tetracetic acid (TITRA) and its derivatives,
vi) triethylenetetramine hexaacetic acid (TTHA) and its derivatives,
vii) 1,4,7-triazacyclononane-1-glutaric acid-4,7-diacetic acid (NODAGA) and its derivatives, and
viii) 1,4,7-triazacyclononane-1-succinic acid-4,7-diacetic acid (NODASA) and its derivatives, and
L is a linker which separates X and Aa8, and said linker L is selected from the group consisting of
-Aa6-Aa7-, wherein X is coupled to Aa6 via the ε-NH$_2$ of the lateral chain of Aa6, or
-L1-Aa6-Aa7-, wherein X is coupled to L1, and L1 is coupled to Aa6 via the ε-NH$_2$ of the lateral chain of Aa6 or via the α-NH2 of Aa6,
wherein
Aa6 is selected from the group consisting of (D)Lys, and (L)Lys,
Aa7 is selected from the group consisting of (L)Pro, and (D)Pro,
and L1 is —NH—(CH$_2$)$_n$—CO— wherein n is from 1 to 5, and
an acetyl group is coupled to the remaining NH$_2$ of Aa6,
and wherein
said analogue, when in solution at physiological pH and at physiological temperature, has at most two positive charges.

2. The neurotensin analogue, or the salt thereof, according to claim 1, wherein Aa8 is NMe-(L)Arg, and Aa12 is (L)Tle.

3. The neurotensin analogue, or the salt thereof, according to claim 1, wherein the neurotensin analogue is selected from the group consisting of the following formulas:

4. A pharmaceutical composition comprising the neurotensin analogue according to claim 1 and a pharmaceutically acceptable carrier.

5. The neurotensin analogue according to claim 1, further comprising a detectable element which forms a complex with the poly(aminocarboxylate) chelating moiety X, wherein the detectable element is selected from the group consisting of $^{111}$In, $^{67}$Ga, $^{68}$Ga, $^{64}$Cu and $^{44}$Sc.

6. The neurotensin analogue according to claim 5, wherein said detectable element is $Gd^{3+}$.

7. The neurotensin analogue according to claim 5, wherein said detectable element is $Eu^{3+}$.

8. The neurotensin analogue according to claim 1, further comprising a cytotoxic element that forms a complex with the chelating moiety X, wherein said cytotoxic element is selected from the group consisting of $^{90}$Y, $^{177}$Lu, $^{67}$Cu, $^{47}$Sc, $^{212}$Bi, $^{213}$Bi, $^{226}$Th, $^{111}$In and $^{67}$Ga.

9. The neurotensin analogue, or the salt thereof, according to claim 1, wherein X represents a poly(aminocarboxylate) chelating moiety selected from the group consisting of: diethylenetriamine pentaacetic acid (DTPA), S-2(4-Aminobenzyl)-diethylenetriamine pentaacetic acid (p-NH2-Bn-DTPA), (R)-2-Amino-3-(4-aminophenyl)propyl]-trans-(S, S)-cyclohexane-1,2-diamine-pentaacetic acid, [(R)-2-amino-3-(4-isothiocyanatophenyl)propyl]-trans-(S,S)-cyclohexane-1,2-diamine-pentaacetic acid, and 2-(4-Isothiocyanatobenzyl)-diethylenetriaminepentaacetic acid (p-SCN-Bn-DTPA).

10. The neurotensin analogue, or the salt thereof, according to claim 1, wherein X represents a poly(aminocarboxylate) chelating moiety selected from the group consisting of: 1,4,7,10-tetraazacyclododecane-1,4,7,10-tetraacetic acid (DOTA), S-2-(4-aminobenzyl)-1,4,7,10-tetraazacyclo-dodecane tetraacetic acid (p-aminobenzyl-DOTA), and S-2-(4-Isothiocyanatobenzyl)-1,4,7,10-tetraazacyclododecane-tetraacetic acid (p-SCN-Bn-DOTA).

11. The neurotensin analogue, or the salt thereof, according to claim 1, wherein X represents a poly(aminocarboxylate) chelating moiety selected from the group consisting of: 1,4,7-triazacyclononane-1,4,7-triacetic acid (NOTA), S-2-(4-aminobenzyl)-1,4,7-triazacyclononane-1,4,7-triacetic acid (p-NH2-Bn-NOTA) and S-2-(4-isothiocyanatobenzyl)-1,4,7-triazacyclononane-1,4,7-triacetic acid (p-SCN-Bn-NOTA).

* * * * *